United States Patent [19]

Black et al.

[11] Patent Number: 5,416,013
[45] Date of Patent: May 16, 1995

[54] INTERLEUKIN 1β PROTEASE AND INTERLEUKIN 1β PROTEASE INHIBITORS

[75] Inventors: Roy A. Black; Paul R. Sleath; Shirley R. Kronheim, all of Seattle, Wash.

[73] Assignee: Sterling Winthrop Inc., Malvern, Pa.

[21] Appl. No.: 203,716

[22] Filed: Feb. 28, 1994

Related U.S. Application Data

[63] Continuation of Ser. No. 750,644, Aug. 30, 1991, abandoned, which is a continuation-in-part of Ser. No. 656,759, Feb. 13, 1991, abandoned, and a continuation-in-part of Ser. No. 505,298, Apr. 4, 1990, abandoned.

[51] Int. Cl.$^6$ .................. C12N 9/64; C12N 15/57
[52] U.S. Cl. ......................... 435/226; 495/219; 536/23.2; 530/351
[58] Field of Search ............... 435/219, 226; 530/351; 536/23.2

[56] References Cited

PUBLICATIONS

Black R. A., et al. (1988) J. Biol. Chem. 263 (19), 9437–9442.
Suggs, S. V., et al, (1981) Proc. Natl. Acad. Sci. USA, 78(11), 6613–6617.
Cheremisinoff, et al. (ed) (1985) Biotechnology Applications and Research, Technomic Pub. Co. Inc, pp. 21, 541–557.
Black, R. A., et al. (1989) Febs Lett. 247 (2), 386–390.
Black, R. A., et al. (1989) J. Biol. Chem. 264 (10), 5323–5326.
Young, R. A. et al, (1983) Science 232, 778–782.
Lee, C. C., et al. (1988) Science 239, 1288–1291.

*Primary Examiner*—Charles L. Patterson, Jr.
*Attorney, Agent, or Firm*—Doreen M. Wells; Gilbert W. Rudman; William J. Davis

[57] ABSTRACT

There is disclosed an isolated polypeptide and derivatives thereof having protease biological activity for human precursor IL-1β and for a substrate comprising:

$$R_1 - Asp - R_2 - R_3$$

wherein $R_1$ and $R_3$ are independently any D or L isomer amino acid, $R_2$ is Ala or Gly, and wherein the specific protease cleavage site is between Asp and $R_2$. Inhibitor compounds, compositions and methods for inhibiting Interleukin 1β protease activity are also disclosed. The inhibitor compounds comprise an amino acid sequence of from 1 to about 5 amino acids having an N-terminal blocking group and a C-terminal Asp residue connected to an electronegative leaving group, wherein the amino acid sequence corresponds to the sequence Ala-Tyr-Val-His-Asp.

3 Claims, 4 Drawing Sheets

```
Lys Pro Lys Val Ile Ile Gln Ala Cys Arg Gly Asp Ser Pro Gly Val Val Trp Phe Lys Asp Ser Val Gly   300
AAA CCG AAG GTG ATC ATC CAG GCC TGC CGT GGT GAC AGC CCT GGT GTG GTG TGG TTT AAA GAT TCA GTA GGA   917
Val Ser Gly Asn Leu Ser Leu Pro Thr Glu Thr Glu Phe Glu Asp Ala Ile Lys Lys Ala His Ile Glu Lys   325
GTT TCT GGA AAC CTA TCT TTA CCA ACT GAA ACT GAG TTT GAG GAT GCT ATT AAG AAA GCC CAC ATA GAG AAG   992
Asp Phe Ile Ala Phe Cys Ser Ser Thr Pro Asp Asn Val Ser Trp Arg His Pro Thr Met Gly Ser Val Phe Ile   350
GAT TTT ATC GCT TTC TGC TCT TCC ACA GAT AAT GTT TCT TGG AGA CAT CCC ACA ATG GGC TCT GTT TTT ATT   1067
Gly Arg Leu Ile Glu His Met Gln Glu Tyr Ala Cys Ser Cys Asp Val Glu Glu Ile Phe Arg Lys Val Arg Phe   375
GGA AGA CTC ATT GAA CAT ATG CAA GAA TAT GCC TGT TCC TGT GAT GTG GAG GAA ATT TTC CGC AAG GTT CGA TTT   1142
Ser Phe Glu Gln Pro Asp Gly Arg Ala Gln Met Pro Thr Thr Glu Arg Val Thr Leu Thr Arg Cys Phe Tyr Leu   400
TCA TTT GAG CAG CCA GAT GGT AGA GCG CAG ATG CCC ACC ACT GAA AGA GTG ACT TTG ACA AGA TGT TTC TAC CTC   1217
Phe Pro Gly His End                                                                                    404
TTC CCA GGA CAT TAA AATAAGGAAACTGTATGAATGTCGCGGGCAGGAAGTGAAGAGATCGTTCTGTAAAAGGTTTTTGAATTATGTCTGCT   1311
GAATAATAAACTTTTTTTGAAATAATCTGGTAGAAAATGAAAAAAAAAAAAAA--3'                                            1373
```

FIG. 2

Met Ala Glu Val Pro Glu Leu Ala Ser Glu Met Met Ala Tyr Tyr Ser
                                     10
Gly Asn Glu Asp Asp Leu Phe Phe Glu Ala Asp Gly Pro Lys Gln Met
                20                                   30
Lys Cys Ser Phe Gln Asp Leu Asp Leu Cys Pro Leu Asp Gly Gly Ile
                            40
Gln Leu Arg Ile Ser Asp His His Tyr Ser Lys Gly Phe Arg Gln Ala
    50                                           60
Ala Ser Val Val Val Ala Met Asp Lys Leu Arg Lys Met Leu Val Pro
                    70                                       80
Cys Pro Gln Thr Phe Gln Glu Asn Asp Leu Ser Thr Phe Phe Pro Phe
                                    90
Ile Phe Glu Glu Glu Pro Ile Phe Phe Asp Thr Trp Asp Asn Glu Ala
                100                                      110
Tyr Val His Asp Ala Pro Val Arg Ser Leu Asn Cys Thr Leu Arg Asp
                            120
Ser Gln Gln Lys Ser Leu Val Met Ser Gly Pro Tyr Glu Leu Lys Ala
    130                                          140
Leu His Leu Gln Gly Gln Asp Met Glu Gln Gln Val Val Phe Ser Met
                        150                                  160
Ser Phe Val Gln Gly Glu Glu Ser Asn Asp Lys Ile Pro Val Ala Leu
                                170
Gly Leu Lys Glu Lys Asn Leu Tyr Leu Ser Cys Val Leu Lys Asp Asp
            180                                      190
Lys Pro Thr Leu Gln Leu Glu Ser Val Asp Pro Lys Asn Tyr Pro Lys
                            200
Lys Lys Met Glu Lys Arg Phe Val Phe Asn Lys Ile Glu Ile Asn Asn
    210                                          220
Lys Leu Glu Phe Glu Ser Ala Gln Phe Pro Asn Trp Tyr Ile Ser Thr
                        230                                  240
Ser Gln Ala Glu Asn Met Pro Val Phe Leu Gly Gly Thr Lys Gly Gly
                                250
Gln Asp Ile Thr Asp Phe Thr Met Gln Phe Val Ser Ser
            260                                  269

INTERLEUKIN 1β PROTEASE AND INTERLEUKIN 1β PROTEASE INHIBITORS

CROSS REFERENCE TO RELATED APPLICATIONS

This is a continuation of copending application Ser. No. 07/750,644 filed on Aug. 30, 1991, now abandoned which is a continuation in part of copending U.S. Application Ser. No. 07/505,298, filed April 4, 1990, now abandoned, and of copending U.S. Application Ser. No. 656,759, now abandoned, filed Feb. 13, 1991.

TECHNICAL FIELD OF THE INVENTION

This invention relates to an interleukin 1β protease enzyme (IL-1β pro) having biological activity to cleave inactive precursor interleukin-1β (IL-1β) polypeptides into active mature IL-1β polypeptides. More specifically, the invention provides an isolated IL-1β pro polypeptide and derivatives thereof that are capable of cleaving a particular amino acid sequence, including the amino acid sequence at the N-terminus of human IL-1β. The present invention further provides a group of compounds that can inhibit IL-1β pro activity and thereby function as IL-1 antagonists.

BACKGROUND OF THE INVENTION

Interleukin 1β (IL-1 β) is a 17.5 kDa polypeptide hormone synthesized and secreted by stimulated monocytes. The initial translation product of IL-1β is a larger 31 kDa biologically inactive precursor polypeptide. The N-terminus of biologically active, mature IL-1β derived from human activated monocytes has been characterized by an N-terminal amino acid sequence beginning with Ala-Pro. See, for example, European Patent Application EP-A 0165654 and March et al., Nature (London) 315:641-47 (1985) for sequence information of human IL-1β.

Many physiological actions and biological activities of IL-1 have been identified. IL-I biological activity is often determined by assaying for stimulation of thymocyte proliferation or by measuring interleukin-2 (IL-2) biological activity. IL-I activities include stimulation of B-lymphocyte maturation, lymphocyte proliferation, stimulation of fibroblast growth and induction of acute-phase protein synthesis by hepatocytes.

Other biological activities have been attributed to IL-1 polypeptides. These include control of differentiation and activation of lmphocytes, stimulation of lymphokine and prostaglandin production, promotion of inflammation, induction of acute phase proteins, stimulation of bone resorption, and alteration of the level of iron and zinc in blood. Moreover, it has recently been found that IL-1 can stimulate the hypothalamus-pituitary-adrenal axis, suggesting that IL-1 is integrated in the complex neuroendocrine network that controls homeostasis. This is further supported by the finding that administration of low doses of IL-I to normal mice results in both a several-fold elevation of glucocorticoid output and in a long-lasting blood glucose concentration increase.

The N-terminal Ala residue of human mature IL-1β is in the 117 position and an Asp residue is in the 116 position counting from the N-terminus of human precursor IL-1β polypeptide. Mature IL-1β consists of the C-terminal 153 residues of the precursor polypeptide.

Maturation and release of mature IL-1β from macrophages does not proceed by conventional means normally associated with most secretory proteins because the precursor IL-1β polypeptide lacks a hydrophobic signal sequence. Further, IL-1β is not associated with a membrane-bound compartment in monocytes. [Singer et al., J. Exp. Med. 167:389-407 (1988)]. Most secretory proteins are characterized by the presence of a hydrophobic stretch of amino acids called a signal sequence. The signal sequence directs the translocation of the protein across the membrane of the endoplasmic reticulum during protein synthesis. The protein is subsequently ushered out of the cell via exocytosis. Most secreted proteins have a signal sequence at the amino terminal that is removed upon translocation. Other proteins, such as ovalbumin, have an internal signal sequence that is not removed upon translocation. Both precursor forms of IL-1α and IL-1β (March et al.) lack any region (either amino terminal or internal) with sufficient hydrophobicity and length to qualify as a signal sequence.

A further indication of an unusual maturation pathway for IL-1β is the absence of a pair of basic amino acids near the N-terminus of the mature polypeptide. The amino acid sequence Tyr-Val-His-Asp- precedes the N-terminal Ala-Pro of the mature human IL1B polypeptide. Moreover, Young et al., J. Cell Bio., 107:447-56 (1988) found that fibroblasts transfected with cDNA coding for precursor IL-1β were unable to process the precursor polypeptide into mature IL-1β. Instead, the transfected fibroblasts produced high levels of inactive precursor polypeptide. The results reported by Young et al. are consistent with other reports for other cell types, including T cells, epidermal cells and B cells.

Hazuda et al., J. Biol. Chem., 263:8473-79 (1988) have reported that both the precursor and mature forms of IL-1β appear in the supernatants of activated monocytes with little or no preference. Hazuda et al. suggest that IL-1β processing is "intimately coordinated" with secretion.

There have been several attempts to characterize or isolate the system responsible for processing IL-1β from its translated precursor form to its active mature form. Black et al., J. Biol. Chem., 263:9437-42 (1988) [Black et al. I] suggest that the cleavage pattern of precursor IL-1β is affected by myeloid cell membranes and results from the action of a plurality of proteases which act as an IL-1β processing system. A subsequent article by Black et al., J. Biol. Chem., 264:5323-26 (1989) [Black et al. II] describes a single protease that cleaves IL-1β between His[115] and Asp[116], one residue upstream form the N-terminal Ala[117] of mature IL-1β. Thus, the protease described in Black et al. II generates a form of IL-1β one amino acid longer than the mature IL-1β purified from monocyte cultures. Black et al. II suggests that there may be an aminopeptidase in human blood that removes the N- terminal asparate residue to complete the processing.

Kostura et al., Proc. Nat Acad Sci. USA, 86:5227-31 (1989) refers to a protease with a similar cleavage pattern but "qualitatively different" from the protease described in Black et al. II. The Kostura et al. protease is characterized as being located in cytosol of monocytic cells. However, Kostura et al. did not further define or isolate the responsible polypeptide.

Finally, Black et al., FEBS Lett., 247:386-90 (1989) [Black et al. III] refer to a protease that generates mature IL-1β from the precursor polypeptide and is characterized by being inhibited by iodoacetate and N- ethylmaleimide. Black et al. III attempted to purify their protease approximately 500 fold by a process starting by freeze-thawing cell lysates from THP-1 cells (ATTC) four times. Black et al. III centrifuged the lysates for 20 minutes at 36,590×g. The supernatant was applied to a DEAE-Sephacel column equilibrated with 10 mM Tris-HCl (pH 8.1) and 5 mM dithiothreitol. The protease was eluted with 80–140 mM NaCl. The eluted material was diluted 1:5 with a buffer of 10 mM Tris-HCl (pH 8.1) and 5 mM dithiothreitol and applied to a procion red agarose column. The protease was eluted with 0.5–0.8 M NaCl, concentrated 20-fold in a Centriprep-10 concentrator, and then subjected to get filtration with Sephadex G-75. This procedure described in Black et al. III failed to demonstrate whether the protease activity was due to a single polypeptide or a group of processing enzymes.

Therefore, there is a need in the art to obtain the isolated system or single protease polypeptide responsible for processing precursor IL-1$\beta$ into its mature and biologically active form. The protease functions as an IL-1 agonist to increase IL-1 biological activity in vivo. Moreover, the isolated protease is useful for improving wound healing, treating arthritis, and treating or preventing the onset of autoimmune diseases, such as insulin dependent diabetes melitus, lupus disorders, Graves' disease, Hashimotos disease, and the detrimental side effects of radiation treatment.

Further, isolation and characterization of the protease responsible for processing precursor IL-1$\beta$ into its biologically active form aids in designing inhibitors for IL-1$\beta$ processing, because the availability of large quantities of IL-1$\beta$ pro serves as a useful screening vehicle for finding compounds having IL-1 antagonist activity. Such IL-1 antagonists or IL-1$\beta$ pro inhibitors are useful for treating inflammation and transplantation rejection.

A number of protease inhibitors specific for other protease activities have been described and reported in the literature. See, e.g., U.S. Pat. Nos. 4,644,055, 4,636,492 and 4,652,552. None of these previously reported protease inhibitors are specific for interleukin 1$\beta$ protease activity. None of the previously described protease inhibitors are effective in inhibiting the activity of interleukin 1$\beta$ protease. Therefore, there is a need for a specific IL-1$\beta$ pro inhibitor that can prevent the cleavage of preIL-1$\beta$ into biologically active IL-1$\beta$. Such an inhibitor can function as an IL-I antagonist. This invention provides IL-I antagonists that prevent the formation of biologically active IL-1$\beta$.

SUMMARY OF THE INVENTION

The present invention is directed to an isolated polypeptide having proteolytic activity for a specific protease cleavage site, wherein the protease activity is specific for a substrate peptide having an amino acid sequence comprising:

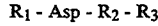

wherein $R_1$ and $R_3$ are independently any D or L isomer amino acid, $R_2$ is Ala or Gly, and wherein the specific protease cleavage site is between Asp and $R_2$. Preferably, the substrate peptide is at least eight amino acids in length. The isolated polypeptide is called the interleukin 1$\beta$ protease (IL-1$\beta$ pro) because it cleaves precursor IL-1$\beta$ polypeptide to yield mature IL-1$\beta$ polypeptide at a cleavage site between the Asp 116 and Ala 117 residues. This region of precursor IL-1$\beta$ corresponds to a species within the genus of protease cleavage sites described herein.

IL-1$\beta$ pro is further characterized by a cDNA (Seq. I.D. No. 1) and amino acid sequence (Seq. I.D. No. 2) in FIG. 1. Full length (precursor) IL-1$\beta$ pro comprises 404 amino acids. Purified IL-1$\beta$ pro begins with the Asn-Pro-Ala-Met-Pro sequence beginning with amino acid 120. However, molecular weight determination indicates that the C-terminus of the mature IL-1$\beta$ pro enzyme is from about amino acid 278 to about amino acid 315. The present invention comprises an isolated IL-1$\beta$ pro polypeptide or a derivative, analog, or allelic variant thereof displaying biological activity to proteolytically cleave human precursor IL-1$\beta$ polypeptide at a cleavage site between the Asp 116 and Ala 117 residues.

Figure 1A:
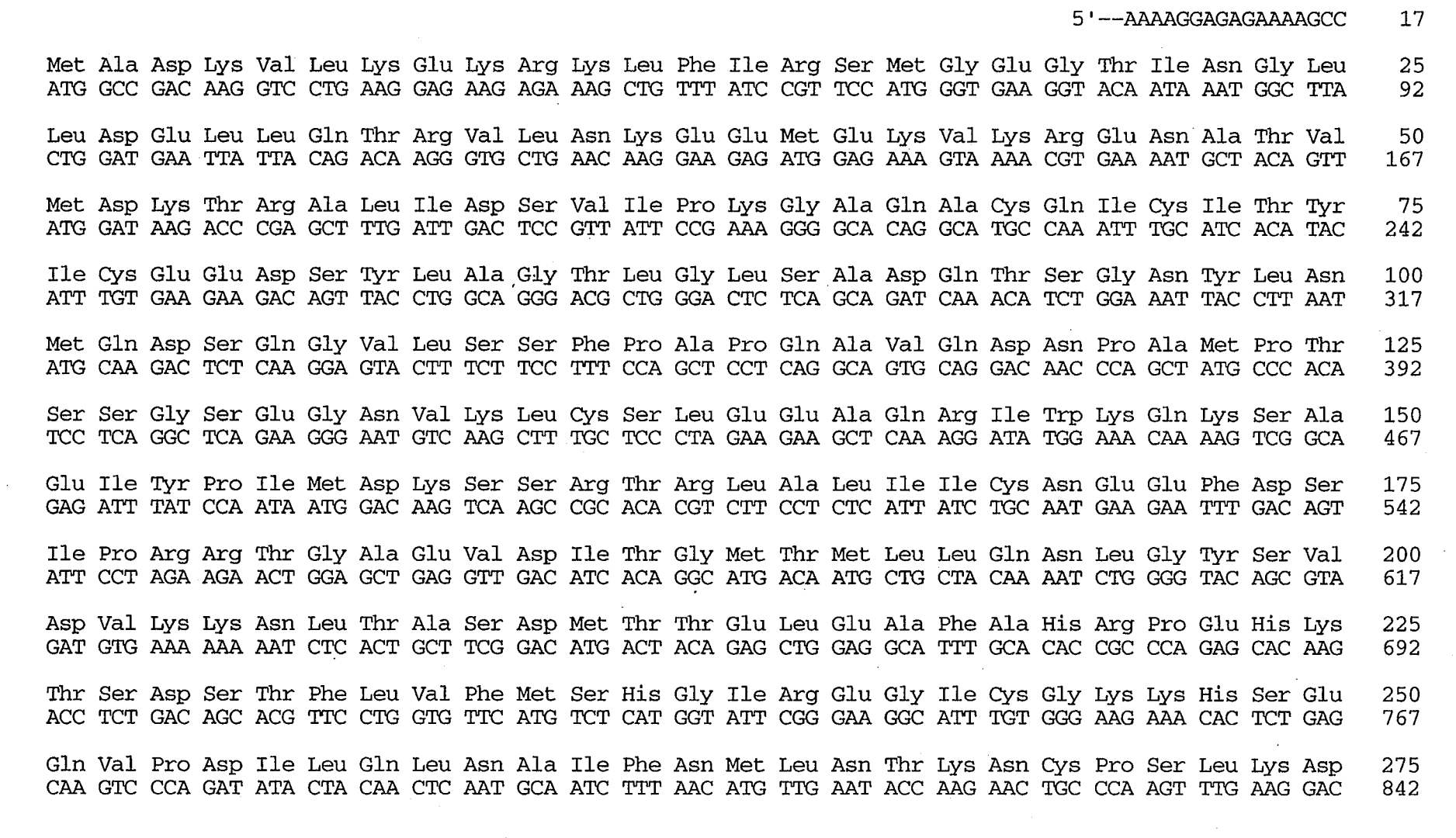

FIG. 1 also shows a nucleotide sequence encoding a 404 amino acid polypeptide having IL-1$\beta$ pro biological activity. The present invention further comprises an isolated DNA sequence encoding IL-1$\beta$ pro or a derivative, analog or allelic variant thereof displaying biological activity to proteolytically cleave human precursor IL-1$\beta$ polypeptide at a cleavage site between the Asp 116 and Ala 117 residues. The isolated DNA sequence is selected from the group consisting of the nucleotide sequences in FIG. 1 beginning at nucleotide 1 and extending to nucleotide 1232, beginning at nucleotide 375 and extending to nucleotide 1232, beginning at nucleotide 375 and extending to a nucleotide from about 851 to about 962, DNA sequences which detectably hybridize to the FIG. 1 sequence from nucleotide 1 to nucleotide 1232 and encode a polypeptide displaying biological activity to proteolytically cleave human precursor IL-1$\beta$ polypeptide at a cleavage site between the Asp 116 and Ala 117 residues, and DNA sequences which, due to degeneracy of the genetic code, encode a mammalian IL-1$\beta$ pro polypeptide encoded by any of the foregoing DNA inserts and sequences.

The present invention further comprises a recombinant expression vector comprising an isolated DNA sequence as described herein and a host cell which comprises the recombinant expression vector.

The present invention also provides substituted peptide inhibitor compounds comprising an amino acid sequence of from 1 to about 5 amino acids, having an N-terminal protecting group and a C-terminal Asp residue connected to an electronegative leaving group. Preferably, the amino acid sequence corresponds to at least a portion of the amino acid sequence Ala-Tyr-Val-His-Asp.

The inhibitor compounds of the present invention have the formula:

Where Z is an N-terminal protecting group; $Q_2$ is 0 to 4 amino acids such that the sequence $Q_2$-Asp corresponds to at least a portion of the sequence Ala-Tyr-Val-His-Asp, residues 112 to 116 of sequence listing I.D. No. 3; and $Q_1$ comprises an electronegative leaving group. Z is preferably $C_1$-$C_6$ alkylketone, benzyl, acetyl, alkoxycarbonyl, benzloxycarbonyl or $C_1$-$C_6$ alkylcarbonyl. More preferably, Z is t-butoxycarbonly (t-Boc), acetyl carbonyl or benzyloxycarbonyl (Cbz).

$Q_1$ is preferably $C_1$-$C_3$ alkyl, an aldehyde diazomethyl ketone or halomethyl ketone. More preferably, $Q_1$ is an aldehyde or fluoromethyl ketone.

The present invention further provides reversible and irreversible IL-1β pro inhibitors. Irreversible inhibitors are inhibitor compounds comprising an amino acid sequence of from 1 to about 5 amino acids having an N-terminal protecting group and a C-terminal Asp residue connected to a diazomethyl ketone or a halomethyl ketone, wherein the amino acid sequence corresponds to at least a portion of the sequence Ala-Tyr-Val-Mis-Asp, residues 112 to 116 of Seq. I.D. No. 3.

Reversible IL-1β inhibitors are compounds comprising an amino acid sequence of from 1 to about 5 amino acids having an N-terminal protecting group and a C-terminal Asp residue connected to an aldehyde moiety, wherein the amino acid sequence corresponds to at least a portion of the sequence Ala-Tyr-Val-His-Asp, residues 112 to 116 of Seq. I.D. No. 3.

The present invention also provides a method of inhibiting the physiological actions of interleukin 1β in a mammal in need of such treatment, comprising administering to said mammal an effective amount of a compound of the formula:

$$Z-Q_2-Asp-Q_1$$

where Z is an N-terminal protecting group; $Q_2$ is 0 to 4 amino acids such that the sequence $Q_2$-Asp corresponds to at least a portion of the sequence Ala-Tyr-Val-His-Asp, residues 112 to 116 of Seq. I.D. No. 3; and $Q_1$ comprises an electronegative leaving group.

In a preferred embodiment, $Q_1$ is a fluoromethyl ketone and inhibition is irreversible. In another preferred embodiment, $Q_1$ is an aldehyde moiety and inhibition is reversible.

The present invention still further provides a pharmaceutical composition comprising a physiologically acceptable carrier and a compound comprising an amino acid sequence of from 1 to about 5 amino acids having an N-terminal protecting group and a C-terminal Asp residue connected to an electronegative leaving group, wherein said amino acid sequence corresponds to at least a portion of the sequence Ala-Tyr-Val-His-Asp, residues 112 to 116 of Seq. I.D. No. 3.

The present invention still further provides a method of treating inflammation associated with autoimmune disease in a mammal in need of such treatment comprising administering to said mammal an effective anti-inflammatory amount of a compound comprising an amino acid sequence of from 1 to about 5 amino acids having an N-terminal protecting groups and a C-terminal Asp residue connected to an electronegative leaving group, wherein said amino acid sequence corresponds to at least a portion of the sequence Ala-Tyr-Val-His-Asp, residues 112 to 116 of Seq. I.D. No. 3.

The present invention further comprises a method for treating arthritis, a method for treating an autoimmune disease in a susceptible individual, a method for improving wound healing, and a method for reducing the detrimental side effects of radiation treatment. All of the methods comprise administering a therapeutically effective amount of an isolated IL-1β protease or a biologically active derivative thereof in a suitable pharmaceutical carrier.

BRIEF DESCRIPTION OF THE DRAWINGS

In the drawings forming a portion of this disclosure:

FIGS. 1A-1B shows the DNA (Seq. I.D. No. 1) and corresponding amino acid sequence (Seq. I.D. No. 2) for a polypeptide having IL-1β pro biological activity and corresponding to human mature IL-1β pro or a biologically active fragment thereof.

FIG. 2 is the amino acid sequence of preIL-I β (Seq. I.D. No. 3), as published by March et al., Nature (London), 315(6021):641–647 (1985). The amino acid residues are numbered (underneath the sequence) beginning with the initiator methionine.

DETAILED DESCRIPTION OF THE INVENTION

Interleukin 1β Protease

Figure 3:
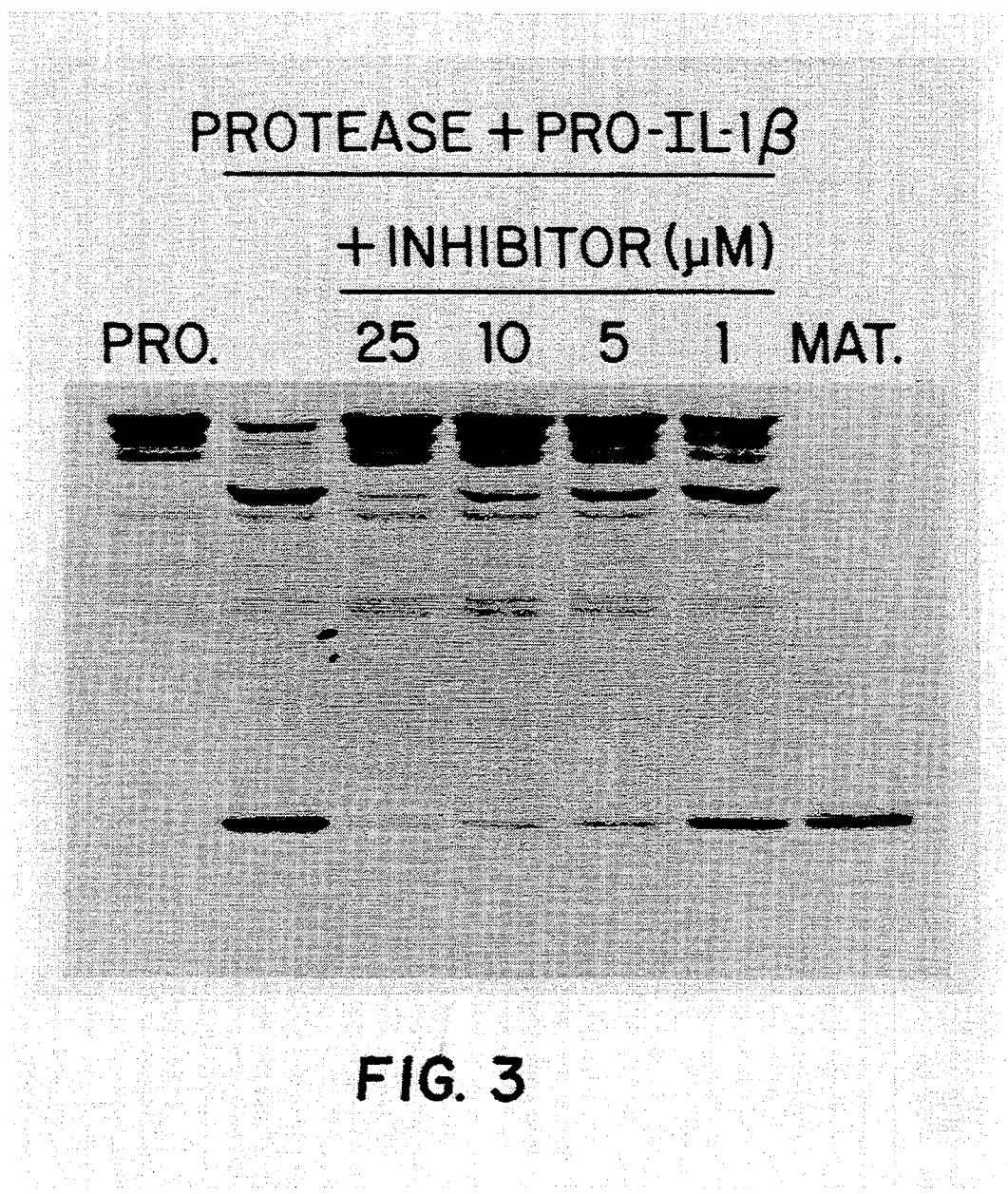
FIG. 3 shows a Western Blot analysis of products generated by IL-1β pro in the presence and absence of the IL-1β pro inhibitor Boc-Asp-CH$_2$F. Products were subjected to SDS-PAGE, transferred to nitrocellulose, and probed with an antibody raised against the COOH terminus of mature IL-1β. Lane 3, preIL-1β incubated with 25 μM of inhibitor; lane 4. preIL-1β incubated with 10 μM of inhibitor; lane 5,. preIL-1β incubated with 5 μM inhibitor, lane 6, preIL-1β incubated with 1 μM inhibitor.

Utilizing polymerase chain reaction (PCR) procedures and other techniques, we have isolated, purified, characterized, and expressed a mammalian IL-1β pro polypeptide and active fragments thereof.

The availability of abundant quantities of a recombinant IL-1β pro enzyme has further allowed us to find inhibitor compounds capable of inhibiting IL-1β pro activity and thereby function as IL-1 antagonists. Further, use of IL-1β pro has IL-1 agohist activity. Thus, the invention relates to mammalian IL-1β pro polypeptides, derivatives, analogs and allelic variants thereof having proteolytic activity for a substrate peptide having an amino acid sequence comprising:

$$R_1-Asp-R_2-R_3$$

wherein $R_1$ and $R_3$ are independently any D or L isomer amino acid, $R_2$ is Ala or Gly, and wherein the specific protease cleavage site is between Asp and $R_2$. Preferably, the substrate peptide is at least eight amino acids in length. Most preferably, $R_2$ is Gly. Mammalian IL-1β pro is preferably a human IL-1β pro and has substrate specificity for a substrate peptide having the amino acid sequence described herein. Preferably, the human IL-1β pro polypeptide or derivative thereof is a polypeptide having biological activity that cleaves human precursor IL-1β polypeptide to yield human mature IL-1β polypeptide.

IL-1β pro is further characterized by the cDNA (Seq. I.D. No. 1) and amino acid sequence (Seq. I.D. No. 2) in FIG. 1. Full length (precursor) IL-1β pro comprises 404 amino acids. Purified IL-1β pro begins with the Asn-Pro-Ala-Met-Pro sequence beginning with amino acid 120. However, the molecular weight determination indicates that the C-terminus of the mature enzyme is from about amino acid 278 to about amino acid 315. The present invention comprises an isolated IL-1β pro polypeptide or a derivative, analog, or allelic variant thereof displaying biological activity to proteolytically cleave a human precursor IL 1β polypeptide at a cleavage site between the Asp 116 and Ala 117 residues. For the purposes of this application, the term "IL-1β pro" shall encompass the amino acid sequence shown in FIG. 1, plus all allelic variants, derivatives, analogs and fragments of this sequence that display IL-1β pro biological activity.

IL-1β pro biological activity is determined, for example, by assaying for IL-1 activity with a precursor IL-1β polypeptide. Precursor IL-1β is inactive, while mature IL-1β is an active IL-1 polypeptide. A method for measuring IL-1β pro activity is described in Black et al. II. Briefly, this method provides approximately five microliters of precursor IL-1β (pre IL-1β) (10-50 β g/ml prepared as described in Black et al. I) incubated with 10 μl of IL-1β pro polypeptide or another substance suspected of having IL-1β pro biological activity. The incubation proceeds for approximately one hour at approximately 37° C. and is terminated by the addition of 15 μl of 2×SDS sample buffer followed by boiling for five minutes. The boiled sample is electrophoresed on a SDS-polyacrylamide gel and placed onto a Western blot using an IL-1β C-terminal-specific monoclonal antibody, such as 16F5 described in Black et al. I.

FIG. 1 also shows a nucleotide sequence encoding a 404 amino acid sequence having IL-1β pro biological activity. The present invention further comprises an isolated DNA sequence encoding IL-1β pro or a derivative, analog or allelic variant thereof displaying biological activity to proteolytically cleave a human precursor IL-1β polypeptide at a cleavage site between the Asp 116 and Ala 117 residues. The isolated DNA sequence is selected from the group consisting of the nucleotide sequences in FIG. 1 beginning at nucleotide 1 and extending to nucleotide 1232, beginning at nucleotide 375 and extending to nucleotide 1232, beginning at nucleotide 375 and extending to a nucleotide from about 851 to about 962, DNA sequences which detectably hybridize to the FIG. 1 sequence from nucleotide 1 to nucleotide 1232 and encode a polypeptide displaying biological activity to proteolytically cleave a human precursor IL-1β polypeptide at a cleavage site between the Asp 116 and Ala 117 residues, and DNA sequences which, due to degeneracy of the genetic code, encode a mammalian IL-1β pro polypeptide encoded by any of the foregoing DNA inserts and sequences.

Inventive DNA sequences that detectably hybridize to the FIG. 1 nucleotide sequence from nucleotide 1 to nucleotide 856, hybridize under conditions of high or severe stringency. Severe or high stringency conditions comprise, for example, overnight hybridization at about 68 C. in a 6×SSC solution followed by washing at about 68 C. in a 0.6×SSC solution.

Antisense oligonucleotides can be synthesized (by conventional phosphodiester techniques such as by Synthecell, Rockville, Md.) that are complementary to unique regions of at least 18 bases at the initiation codon (TACCGGCTGTTCCAGGAC, Seq. I.D. No. 4) or (TACCTATTCTGGGCTCGA, Seq. I.D. No. 5) complementary to bases 18-36 and 168 to 196, respectively in FIG. 1, at the N-terminus of mature IL-1β pro (TTGGTCGATACGGGTGT, Seq. I.D. No. 6) complementary to bases 374 to 392 in FIG. 1, at the approximate C terminus after protease cleavage (CACCACACCAAATTTCTA, Seq. I.D. No. 7) complementary to bases 890 to 908 in FIG. 1, or at a region immediately 5' to the termination codon (ATGGAGAAGGGTCCTGTA, Seq. I.D. No. 8) complementary to bases 1205 to 1229 in FIG. 1.

The primary amino acid structure of IL-1β pro or its active fragment thereof may be modified by forming covalent or aggregative conjugates with other chemical moieties, such as glycosyl groups, lipids, phosphate, acetyl groups and the like, or by creating amino acid sequence mutants or derivatives. Covalent derivatives of IL-1β pro are prepared by linking particular functional groups to IL-1β pro amino acid side chains or at the N-terminus or C-terminus of the IL-1β pro polypeptide.

Other derivatives of IL-1β pro within the scope of this invention include covalent or aggregative conjugates of IL-1β pro or its fragments with other proteins or polypeptides, such as by synthesis in recombinant culture as N-terminal or C-terminal fusions. For example, the conjugated polypeptide may be a signal (or leader) polypeptide sequence at the N-terminal region of IL-1β pro polypeptide which co-translationally or post-translationally directs transfer of the IL-1β pro polypeptide from its site of synthesis to a site inside or outside of the cell membrane or wall (e.g., the yeast α-factor leader). IL-1β pro polypeptide fusions can comprise polypeptides added to facilitate purification and identification of IL-1β pro (e.g., poly-His). Further, the amino acid sequence of IL-1β pro can be linked to the peptide Asp-Tyr-Lys-Asp-Asp-Asp-Asp-Lys (Hopp et al. BioTechnology 6:1204 (1988)), which is a highly antigenic sequence and provides an epitope reversibly bound by a specific monoclonal antibody to enable rapid assay and facile purification of the expressed recombinant polypeptide. This specific leader sequence is cleaved by bovine mucosal enterokinase at the residue immediately following the Asp-Lys pairing. Moreover, fusion polypeptides having this leader sequence at its N-terminal may be resistant to degradation in E. coli host cells.

The present invention further includes IL-1β pro polypeptides with or without associated native-pattern glycosylation. IL-1β, pro expressed in yeast or mammalian expression systems (e.g., COS-7 cells) may be similar or significantly different in molecular weight and glycosylation pattern than the native human IL-1β pro polypeptide. This depends upon the choice of expression system. Expression of IL-1β pro polypeptides in bacterial expression systems, such as E. coli, provides non-glycosylated molecules.

Functional mutant analogs of human IL-1β pro can be synthesized, for example, with inactivated N-glycosylation sites by oligonucleotide synthesis and ligation or by site specific mutagenesis techniques. The IL-1β pro derivatives can be expressed in homogeneous, reduced carbohydrate form using yeast expression systems. N-glycosylation sites in eukaryotic polypeptides are characterized by an amino acid triplet Asn-Φ-Ω where Φ is any amino acid except Pro and Ω is Ser or Thr. In this sequence, carbohydrate residues are covalently attached at the Asn side chain.

IL-1β pro analogs or derivatives may also be obtained by mutations of the IL-1β pro DNA sequence. An IL-1β pro mutant derivative, as referred to herein, is a polypeptide substantially homoiogous to IL-1β pro but which has an amino acid sequence different from native IL-1β pro because of a deletion, insertion or substitution.

IL-1β pro is expressed from a mammalian gene, presumably encoded by one or more multi-exon genes. The present invention further includes alternative mRNA constructs which can be attributed to different mRNA splicing events following transcription, and which share regions of identity or similarity with the cDNA's disclosed herein.

Bioequivalent analogs of IL-1β pro polypeptides (defined as polypeptides having IL-1β pro biological activity) can be constructed, for example, by making various substitutions of amino acid residues or sequences, or by deleting terminal or internal residues or sequences not needed for biological activity. For example, Cys residues can be deleted or replaced with other amino acids to prevent formation of incorrect intramolecular disulfide bridges upon renaturation. Other approaches to mutagenesis involve modification of dibasic amino acid residues to enhance expression in yeast systems in which KEX2 protease activity is present.

Generally, substitutions are made conservatively by substituting and amino acid having physiochemical characteristics resembling those of the replaced residue. Further substitutions may be outside of the "core" sequence needed for IL-1$\beta$ pro biological activity. Subunits of IL-1$\beta$ pro may be constructed by deleting terminal or internal residues or sequences. The resulting polypeptide should have IL-1$\beta$ pro biological activity as defined herein.

The terms "IL-1$\beta$ pro", "human IL-1$\beta$ protease" include, but are not limited to, analogs or subunits of IL-1$\beta$ pro which are substantially similar to human IL-1$\beta$ pro and/or which exhibit the substrate-specific proteolytic biological activity associated with IL-1$\beta$ pro as described herein.

The term "substantially similar", when used to describe amino acid sequences, means that a particular sequence may vary from a disclosed reference sequence by one or more substitutions, deletions, or additions. However, the net effect is the same protease biological activity characteristic of the reference human IL-1$\beta$ pro polypeptide. For example, a derivative can have a truncated sequence comprising a "core region" or a sequence of amino acids necessary for the specific protease biological activity characteristic of IL-1$\beta$ pro. Substantially similar IL-1$\beta$ pro derivatives will be greater than about 30% similar to the corresponding sequence of human IL-1$\beta$ pro and have IL-1$\beta$ pro biological activity. Polypeptides having amino acid sequences of lesser degrees of similarity but comparable biological activity (including substrate specificity) are considered to be equivalents. More preferably, the derivative polypeptides will have greater than 80% amino acid sequence homology to human IL-1$\beta$ pro polypeptide.

Percent similarity may be determined, for example, by comparing sequence information using a GAP computer program, version 6.0, available from University of Wisconsin Genetics Computer Group. The GAP program uses the alignment method of Needleman and Wunsch (*J. Mol. Biol*, 48:443 (1970)), as revised by Smith and Waterman [*Adv. Appl. Math*, 2:482 (1981)]. Briefly, the GAP program defines similarity as the number of aligned symbols which are similar, divided by the total number of symbols in the shorter of the two sequences. The preferred default parameters for the GAP program include: (1) a weighted comparison matrix for amino acids [See, Schwartz and Dayhoff, eds. Atlas of Protein Sequence and Structure, National Biomedical Research Foundation, pp. 353–58 (1979)]; (2) a penalty of 3.0 for each gap and an additional 0.10 penalty for each symbol in each gap; and (3) no penalty for end gaps.

"Biologically active" as used herein, refers to IL-1$\beta$ pro biological activity to cleave a particular amino acid sequence at the peptide bond between an Asp residue and an Ala or Gly residue.

"Recombinant" as used herein, means that a polypeptide is derived from recombinant (e.g., microbial or mammalian) expression systems. "Microbial" refers to bacterial or fungal (e.g., yeast) expression systems. As a product, "recombinant microbial" defines a polypeptide produced in a microbial expression system which is substantially free of native endogenous substances. Polypeptides expressed in most bacterial expression systems (e.g., *E. coli*) will be free of glycan. Polypeptides expressed in yeast may have a glycosylation pattern different from that expressed in mammalian cells.

The IL-1$\beta$ pro protease has a highly restricted substrate specificity. Human precursor IL-1$\beta$ polypeptide has an amino acid sequence His-Asp-Ala-Pro for residues 115–118. Human IL-1$\beta$ pro cleaves this sequence between residues 116 and 117 (Asp-Ala) to form human mature IL-1$\beta$ polypeptide. Changing Asp-116 to Ala in a human precursor IL-1$\beta$ polypeptide by site-directed mutagenesis prevented cleavage of the mutant IL-1$\beta$ polypeptide derivative.

Isolated human IL-1$\beta$ pro was able to cleave at its specific substrate site even when the tertiary structure of the substrate precursor IL-1$\beta$ polypeptide was altered by denaturing the substrate polypeptide in boiling water. Precursor human IL-1$\beta$ was denatured by boiling a solution of precursor IL-1$\beta$ for fifteen minutes. Denaturation had little effect on the ability of human IL-1$\beta$ pro to be able to cleave human precursor IL-1$\beta$ into mature IL-1$\beta$. Thus, the tertiary structure of the substrate polypeptide does not significantly contribute to the reaction with the enzyme IL-1$\beta$ pro.

IL-1$\beta$ pro biological activity was determined by a protease assay. As the IL-1$\beta$ pro enzyme is salt sensitive, samples having a salt concentration greater than 50 mM were initially desalted. Samples can be desalted, for example, by applying 100 $\mu$l of sample to a pre-spun 1 ml Biogel P-6DG (Bio-Rad) column, which was equilibrated in 10 mM Tris-HCl, 5 mM dithiothreitol, pH 8.1, and centrifuging for 5 minutes at 1876×g. The assay was conducted by incubating a mixture of five $\mu$l (30 ng) of purified human IL-1$\beta$ precursor and 10 $\mu$l of the sample to be tested for IL-1$\beta$ protease biological activity for 60 minutes at 37 C. A control sample was similarly incubated to check for endogenous IL-1. The control sample mixture contained 5 $\mu$l of 10 mM Tris-HCl, pH 8.1 and 5 mM dithiothreitol instead of IL-1$\beta$ precursor. The control sample incubations were terminated by addition of SDS (sodium dodecyl sulfate) in sample buffer followed by five minutes of boiling.

All incubated assay mixtures were electrophoresed on 0.75 mm-thick SDS, 14% polyacrylamide slab gels, using a discontinuous system, such as the one described in Laemmli, *Nature*, 277:680 (1970). Western blots were performed following electrophoresis by transferring the proteins onto nitrocellulose (Sartorius) and probing using an 20 $\mu$g/ml solution of purified IL-1$\beta$ COOH-terminal-specific monoclonal antibody (i.e., 16F5). The blot was developed using Horseradish Peroxidase Color Developing Reagent (Bio Rad). One hundred ng of purified mature IL-1$\beta$ was used as a control 17,500 dalton marker on the Wester blot.

Human IL-1$\beta$ pro enzyme was obtained and purified from THP-1 cells obtainable from the American Type Culture Collection (ATCC). Approximately 120 liters of cells were cultured and then stimulated for 16 hours with liposaccharide, hydroxyurea and silica as described in Matsushima, *Biochemistry*, 25:3424 (1986). The cells were harvested by centrifugation, washed in Hanks balanced salt solution, and then recentrifuged. The cells were resuspended in 10 mM Tris-HCl, 5 mM dithiothreitol, pH 8.1 at a density of $10^8$ ml. The suspended cells were frozen and thawed three times and the lysates stored at $-80°$ C. until further use. Prior to purification, the lysates were thawed and then centrifuged for 20 minutes at 47,800×g at 4° C. The supernatant was taken for further purification. The freeze-thawing procedure repeated four times released over 50% of the IL-1β pro activity into the supernatant. Additional freeze-thaws did not increase the yield of soluble material.

The human IL-1β pro polypeptide was purified in a six-step process described below. All the chromatography steps were performed at 4° C. using a Pharmacia FPLC System. DEAE-Sephacel, Hydroxyapatite and Blue Agarose gels were pretreated with 0.1% Triton-X-100 and 10% bovine calf serum to prevent non-specific absorption of proteins to the gels. Further, the Blue Agarose column was washed with 8M urea to remove any noncovalently absorbed dye.

1. Approximately 500–600 ml of lysate supernatant was diluted 1:2 in 10 mM Tris-HCl and 5 mM dithiothreitol, pH 8.1 ("buffer A") to reduce ionic strength of the lysate to <20 mM. pH was adjusted to 8.1. The diluted lysate supernatant was applied to a DEAE-Sephacel column (20×4.4 cm, Pharmacia Fine Chemicals), equilibrated with buffer A. The flow rate was 120 ml/hour. The column was washed with two column volumes of buffer A and then eluted with a linear gradient (3 column volumes) ranging from 0 to 300 mM NaCl in buffer A. Fifteen ml fractions were collected, analyzed for IL-1β pro activity and stored for further purification. The IL-1β pro activity was eluted with between 0.07 and 0.13M NaCl. This step removed 79% of the contaminating proteins. The bulk of the contaminating proteins eluted between 0.15 and 0.25M NaCl. This step was further useful in partially removing endogenous mature IL-1β, which eluted between 0.06 and 0.11M NaCl, and endogenous precursor IL-1β which eluted between 0.12 and 0.18 M NaCl.

2. The pooled active fractions from the DEAE column were diluted in 50 mM potassium phosphate buffer, 5 mM dithiothreitol, pH 7.0 ("buffer B"). A 14×3 cm column of hydroxyapatite (HA Ultrogel, IBF Biotechnics) was equilibrated with buffer B. The diluted fractions were applied to the equilibrated hydroxyapatite column at a flow rate of 60 ml/hour. The column was washed with 2 column volumes of buffer B and then eluted with a linear gradient (4 column volumes) ranging from 50–200 mM potassium phosphate. Fractions were collected as 10 ml volumes, analyzed for IL-1β pro activity, and stored for further purification. IL-1β pro eluted between 0.085 and 0.113M potassium phosphate. Forty percent of the contaminating polypeptides eluted before the protease and 40% eluted later than the protease. Further, endogenous mature IL-1β eluted between 0.05 and 0.08M potassium phosphate.

3. A 20×1.6 cm Blue Agarose column (GibcoBRL) was equilibrated with buffer A. Fractions from the hydroxyapatite column with activity were diluted 1:3 in buffer A to reduce ionic strength to 30 mM. This was necessary in order to allow IL-1β pro to bind to the column. Diluted fractions were applied to the Blue Agarose column at a 30 ml/hour rate. The column was washed with three column volumes of buffer A. The proteins were eluted with five column volumes of a linear gradient ranging from 0.1 to 1M NaCl in buffer A. Ten ml fractions were collected, analyzed for IL-1β pro activity and stored for further purification. IL-1β pro was eluted with 0.5 to 0.68M NaCl. Eighty percent of the contaminating proteins were removed in this step, with 20% eluting earlier and the remaining 60% remaining bound to the column.

4. A 95×2.5 cm Sephadex G-75 column (Pharmacia Fine Chemicals) was equilibrated in buffer A and initially calibrated with ferritin (MW 400,000), ovalbumin (MW 43,000), soybean trypsin inhibitor (MW 20,000) and DNP-aspartic acid (MW 300). The Blue Agarose column fractions containing protease activity were pooled and concentrated on a Centriprep-10 concentrator (Amicon) to a volume of approximately 2 ml and then applied to the Sephadex G-75 column. Proteins were eluted with buffer A at a flow rate of 20 ml/hr. Four ml fractions were collected and the fractions containing protease activity were pooled for further purification. IL-1β pro activity was eluted with between 196 and 220 ml. This position is identical to the elution position of soybean trypsin inhibitor, which suggests that human IL-1β pro has a molecular weight of about 20,000 daltons. This step removed over 90% of the contaminating proteins from the preparation. Thus, through the Sephadex step, more than 99.8% of the starting protein contaminants have been separated from IL-1β pro. However, PAGE (polyacrylamide gel electrophoresis) analysis of the fractions still revealed several protein bands that did not correlate with IL-1β pro biological activity.

5. Fractions from the Sephadex column which contained protease activity were pooled and the pool was concentrated on pretreated Centriprep 10 Concentrators to a 5001 µl volume. Since protein concentration of the Sephadex pool was low (<30 µg/ml), pretreatment of the centripreps with bovine serum albumin reduced loss of IL-1β pro activity during concentration. Extensive washing of the treated centripreps prior to use prevented contamination of samples with albumin. Pretreatment was accomplished by centrifuging 15 ml of 1% bovine serum albumin (BSA) in centripreps for 30 minutes, decanting the remaining solution, and washing with 10 mM Tris-HCl. A Mono P5/20 FPLC chromatofocusing column (Pharmacia Fine Chemicals) was equilibrated with 25 mM Tris-acetate and 5 mM dithiothreitol, pH 8.3 buffer. The concentrated solution was mixed (1:1 v/v) with 500 µl of 25 mM Tris-acetate and 5 mM dithiothreitol, pH 8.3 and applied to the Mono P5/20 FPLC column. Proteins were eluted with Polybuffer 96:Polybuffer 74 (3:7) pH 5.0 (Pharmacia) at a 15 ml/hour flow rate. One ml fractions were collected and analyzed for pH and biological protease activity. This chromatofocusing step increased the purity of IL-1β pro a further 100 fold and allowed for the visualization of a single protein band that correlated with IL-1β pro biological activity. IL-1β pro was eluted off the chromatofocusing column between pH 6.95 and 6.70. The fractions were concentrated on BSA-pretreated Centricon Concentrators (Amicon) from 1 µl to 50 µl.

6. The fractions were subjected to electrophoresis on a polyacrylamide gel (PAGE), followed by electroblotting onto polyvinyl difluoride membrane paper (PVDF, Millipore Immobilin-P ®) at 300 mA for 30 minutes. The PVDF membrane was stained with Coomassie Blue. There were five major bands with molecular weights of approximately 45,000, 43,000, 36,000, 22,000 and 18,000 daltons. The 22,000 dalton band correlated with IL-1β pro activity and was sequenced.

The N-terminal sequence of the 22,000 dalton band yielded an amino acid sequence described herein. A mature human IL-1β pro cDNA or an active fragment thereof was cloned using this N-terminal amino acid sequence and a three-stage polymerase chain reaction (PCR) procedure. In the first stage PCR procedure, fully degenerate PCR primers were designed and made from the N-terminal amino acid sequence. The degenerate primers were used to amplify IL-1β pro-specific sequences from a cDNA library prepared from THP-1 cell mRNA. A random primed first strand THP-1 cDNA library was constructed according to supplier instructions (Amersham). A mixed oligonucleotide primed amplification was carried out according to the procedure described in Lee et al. "cDNA Cloning Using Degenerate Primers" in PCR Protocols (Innis, Gelfand, Sninsky and White eds.) Academic Press, Inc. New York pp. 46–53 1990. Primer #1 was designed to cross-hybridize to IL-1β pro DNA (nucleotides 1–17) and to contain an Eco RI restriction site. Primer #1 had the sequence:

5'-GTCGAATTCAA(T/C)CCNGCNATGCCNAC-3, (Seq. I.D. No. 9).

Primer #2 was designed to cross-hybridize to IL-1β pro DNA (complementary to nucleotides 31–47 and contain an Xba I restriction site. Primer #2 had the sequence:

5'-GTCTCTAGAAG(T/C)TTNAC-(A/G)TTNCC(T/C)TC-3'

(Seq. I.D. No. 10).

PCR amplification was performed with thermus aquatius polymerase (Perkin-Elmer Cetus) in 100 μl of buffer for 30 cycles as described in Lee et al., *infra*. A 63 bp amplified fragment was obtained from PCR amplification. This amplified fragment was subcloned into a pGem-4 vector (Promega). DNA sequence analysis of 10 isolates indicated that this fragment encoded the first 16 amino acids of the N-terminus of IL-1β pro as determined by purification and N-terminal sequence analysis.

The second stage of the PCR procedure made Primer 190 3 composed of nucleotides 1–17 (FIG. 1) and a Not I restriction site and Primer 190 4 containing 20 T residues and a Not I restriction site. Primers 190 3 and 190 4 were added to the THP-1 cDNA library described above and PCR amplified for 6 cycles at 94° C. for 1 minute, 50° C. for 1 minute and 72° C. for 1 minute. Southern analysis of the PCR amplified clone using a 17 base oligonucleotide probe (complementary to nucleotides 16–32 in FIG. 1) found a band at approximately 1000 bp that was also found to posses IL-1β pro biological activity. The 1000 bp DNA was gel purified, subjected to a similar second round of PCR and subcloned into pGem-5 for sequencing. The nucleotide sequence of this clone is shown in FIG. 1.

In the third stage of PCR cloning, full length IL-1β pro clones were isolated from a cDNA library prepared from peripheral blood neutrophils. We found that neutrophils expressed IL-1β pro mRNA. We isolated two clones (p48 and p214) with IL-1β pro specific inserts of 1367 and 1360 base pairs, respectively. The DNA sequence shown in FIG. 1 is a composite of all the IL-1β pro clones. The amino acids encoded by all of the IL-1β pro clones we found were identical.

IL-1β pro cDNA is approximately 1373 base pairs in length, including a stretch of A nucleotides corresponding to the poly (A) tail of mRNA. These A residues are preceded by two polyadenylation signals, AATAA, at 1316 and 1335 base pair. The sequence has an open reading frame of 404 amino acids, starting with an initiator Met codon at nucleotide 18 and ending with a termination codon at nucleotide 1230. Initiation of translation could also begin with an in-frame Met codon at nucleotide 66. Both initiator Met codons have consensus Kozak translation initiation sequences. Polypeptides initiated with the Met residue at position 51 also have biological activity.

IL-1β pro is a cytoplasmic enzyme. As the purified enzyme N-terminal amino acid is Asn (120), the protease undergoes N-terminal processing resulting in removal of 119 amino acids or 69 amino acids if the alternate initiator codon is used. Deletion analysis has indicated that at least 107 amino acids are removed from the C-terminus. However, it appears that the full C-terminus is necessary for proper folding of the protease before approximately 107 C-terminal amino acids can be removed to insure biological activity for the protease.

The DNA sequence shown in FIG. 1 was expressed in a mammalian cell (e.g., COS-7 cells). For mammalian cell expression, synthetic oligonucleotide primers were made to amplify the entire coding domain of IL-1β pro. The 5' primer (5'-ATATCGGTACCGCCTCCAG-CATGCCTCCGGCAATGCCCACATC-3,)

(Seq. I.D. No. 11) contained an Asp 718 restriction site and an initiator Met residue fused to the N-terminus of the enzyme (nucleotides 1–20). The 3' primer (5'-CTGCTAGATCTGCCCGCAGACATT-CATACAG-3,)

(Seq. I.D. No. 12)

contains a *Bgl* II restriction site and is complementary to nucleotides 883–902 of FIG. 1. The PCR generated fragment was ligated into pDC303 mammalian vector, as described in Mosley et al., *Cell*, 59:335–348 (1989).

Human IL-1β pro is preferably produced by recombinant DNA techniques. A recombinant DNA expression system inserts a clone encoding human IL-1β pro polypeptide or a derivative thereof with biological activity into an expression vector. The expression vector is inserted into a host cell. The host cell's protein syntheses machinery synthesizes the recombinant human IL-1β pro polypeptide.

Suitable host cells for expression of mammalian IL-1β pro polypeptides or derivatives thereof include prokaryotes, yeast or higher eukaryotic cells under the control of appropriate promoters. Prokaryotes include gram negative or gram positive organisms, for example *E. coli* or bacilli. Suitable prokaryotic hosts cells for transformation include, for example, *E. coli, Bacillus subtilis, Salmonella typhimurium,* and various other species within the genera Pseudomonas, Streptomyces, and Staphylococcus. Higher eukaryotic cells include established cell lines of mammalian origin as described below. Cell-free translation systems could also be employed to produce mammalian IL-1β pro polypeptides or derivatives thereof using RNAs derived from the DNA constructs disclosed herein. Appropriate cloning and expression vectors for use with bacterial, fungal, yeast, and mammalian cellular hosts are described, for example, in Pouwels et al., *Cloning Vectors: A Laboratory Manual*, Elsevier, New York, (1985).

When an IL-1$\beta$ pro polypeptide or derivative thereof is expressed in a yeast host cell, the nucleotide sequence (e.g., structural gene) that codes on expression for an IL-1$\beta$ propolypeptide or derivative thereof may include a leader sequence. The leader sequence enables improved extracellular secretion of translated polypeptide by a yeast host cell.

Alternatively, in a prokaryotic host cell, such as *E. coli,* the IL-1$\beta$ pro polypeptide or derivative thereof may include an N-terminal methionine residue to facilitate expression of the recombinant polypeptide in a prokaryotic host cell. The N-terminal Met may be cleaved from the expressed recombinant IL-1$\beta$ pro polypeptide or derivative thereof. Moreover, prokaryotic host cells may be used for expression and disulfide processing.

The recombinant expression vectors carrying the recombinant IL-1$\beta$ pro structural gene nucleotide sequence or derivative thereof are transfected or transformed into a substantially homogeneous culture of a suitable host microorganism or mammalian cell line. Examples of suitable host cells include bacteria such as *E. coli,* yeast such as *S. crevisiae,* or a mammalian cell line such as Chinese Hamster Ovary (CHO) cells.

Transformed host cells are cells which have been transformed or transfected with IL-1$\beta$ pro or a derivative thereof structural gene nucleotide sequences. Expressed IL-1$\beta$ pro polypeptides will be located within the host cell and/or secreted into culture supernatant, depending upon the nature of the host cell and the gene construct inserted into the host cell. Expression vectors transfected into prokaryotic host cells generally comprise one or more phenotypic selectable markers. A phenotypic selectable marker is, for example, a gene encoding proteins that confer antibiotic resistance or that supply an autotrophic requirement, and an origin of replication recognized by the host to ensure amplification within the host.

Other useful expression vectors for prokaryotic host cells include a selectable marker of bacterial origin derived from commercially available plasmids. This selectable marker can comprise genetic elements of the cloning vector pBR322 (ATTC 37017). pBR322 contains genes for ampicillin and tetracycline resistance and thus provides simple means for identifying transformed cells. The pBR322 "backbone" sections are combined with an appropriate promoter and an IL-1$\mu$ pro structural gene sequence. Other commercially vectors include, for example, pKK223-3 (Pharmacia Fine Chemicals, Uppsala, Sweden) and pGEM-1 (Promega Biotec, Madison, Wis, USA).

Promoter sequences are commonly used for recombinant prokaryotic host cell expression vectors. Common promotor sequences include $\beta$-lactamase (penicillinase), lactose promoter system (Chang et al., Nature, 275:615, 1978; and Goeddel et al., *Nature,* 281:544, 1979), tryptophan (trp) promoter system (Goeddel et al., *Nucl. Acids Res,.* 8:4057, 1980; and EPA 36,776) and tac promoter (Maniatis, Molecular Cloning: A Laboratory Manual, Cold Spring Harbor Laboratory, p.412, 1982). A particularly useful prokaryotic host cell expression system employs a phage $\lambda$ $P_L$ promoter and a cI875ts thermolabile repressor sequence. Plasmid vectors available from the American Type Culture Collection which incorporate derivatives of the $\lambda$ $P_L$ promoter include plasmid pHUB2 (resident in *E. coli* strain JMB9 (ATCC 37092)) and pPLc28 (resident in *E. coli* RR1 (ATCC 53082)).

Human IL-1$\mu$ pro polypeptides and derivative polypeptides may be expressed in yeast host cells, preferably from the *Saccharomyces* genus (e.g., *S. cerevisiae*). Other genera of yeast, such as *Pichia* or *Kluyveromyces,* may also be employed. Yeast vectors will often contain an origin of replication sequence from a 2$\mu$ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase [Hitzeman et al., *J. Biol. Chem.,* 255:2073, (1980)] or other glycolytic enzymes [Hess, et al., *J. Adv. Enzyme Reg.,* 7:149, (1968); and Holland et al., *Biochem.* 17:4900, (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EP-A-73,657.

Yeast vectors can be assembled, for example, using DNA sequences from pBR322 for selection and replication in *E. coli* ($Amp^r$ gene and origin of replication). Other yeast DNA sequences that can be included in a yeast expression construct include a glucose-repressible ADH2 promoter and $\alpha$-factor secretion leader. The ADH2 promoter has been described by Russell et al., [*J. Biol. Chem.,* 258:2674, (1982)] and Beier et al., [Nature, 300:724, (1982)]. The yeast $\alpha$-factor leader sequence directs secretion of heterologous polypeptides. The $\alpha$-factor leader sequence is often inserted between the promoter sequence and the structural gene sequence. [See, e.g., Kurjan et al., *Cell,* 30:933, (1982); and Bitter et al., *Proc. Natl, Acad. Sci. USA,* 81:5330, (1984).] A leader sequence may be modified near its 3′ end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA,* 75:1929, (1978). The Hinnen et al., protocol selects for $Trp^+$ transformants in a selective medium, wherein the selective medium consists of 0.67% yeast nitrogen base, 0.5% casamino acids, 2% glucose, 10 $\mu$g/ml adenine 10 and 20 $\mu$g/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 $\mu$g/ml adenine and 80 $\mu$g/ml muacil. Derepression of the ADH2 promoter occurs when glucose is exhausted from the medium.

Mammalian or insect host cell culture systems could also be employed to express recombinant IL-1$\beta$ pro polypeptide or derivatives thereof. Examples of suitable mammalian host cell lines include the COS-7 lines of monkey kidney cells [Gluzman, *Cell,* 23:175, (1981)], L cells, C127 cells, 3T3 cells, Chinese hamster ovary (CHO) cells, HeLa cells, and BHK cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences in mammalian host cell expression vectors may be provided by viral sources. For example, commonly used mammalian cell promoter sequences and enhancer sequences are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication [Fiers et al., Nature, 273:113, (1978)]. Smaller or larger SV40 fragments may also be used, provided the approximately 250 bp sequence extending from the Hind III site toward the BglI site located in the SV40 viral origin of replication site is included.

Further, mammalian genomic IL-1β pro promoter, control and/or signal sequences may be utilized, provided such control sequences are compatible with the host cell chosen. Exemplary vectors can be constructed as disclosed by Okayama and Berg [Mol. Cell. Biol., 3:280, (1983)].

Purified human IL-1β pro polypeptides or derivatives thereof are prepared by culturing transformed host cells under culture conditions necessary to express IL-1β pro polypeptides or derivatives thereof. The expressed polypeptides are purified from culture media or cell extracts. For example, supernatants from cultured transformed host cells can secrete recombinant IL-1β pro polypeptide into culture media. The IL-1β pro polypeptide or derivative thereof is concentrated using a commercially available protein concentration filter, for example, an Amicon or Millipore Pellicon ultrafiltration unit. Following the concentration step, the concentrate can be applied to a purification matrix. For example, a suitable purification matrix is an IL-1β pro inhibitor or an antibody molecule specific for an IL-1β pro polypeptide or derivative thereof and bound to a suitable support. Alternatively, an anion exchange resin can be employed, for example, a matrix or substrate having pendent diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reverse-phase high performance liquid chromatography (RP-HPLC) steps employing hydrophobic RP-HPLC media, e.g., silica gel having pendant methyl or other aliphatic groups, can be employed to further purify an IL-1β pro polypeptide composition. Some or all of the foregoing purification steps, in various combinations, can also be employed to provide a homogeneous recombinant protein. Alternatively, some or all of the steps used in the purification procedure described herein can also be employed.

Recombinant polypeptide produced in bacterial culture is usually isolated by initial disruption of the host cells, extraction from cell pellets of an insoluble polypeptide, or from the supernatant of a soluble polypeptide, followed by one or more concentration, salting-out, ion exchange or size exclusion chromatography steps. Finally, reverse phase high performance liquid chromatography (RP-HPLC) can be employed for final purification steps. Microbial cells can be disrupted by any convenient method, including freeze-thaw cycling, sonication, mechanical disruption, or use of cell lysing agents.

Transformed yeast host cells generally express IL-1β pro polypeptide as a secreted polypeptide. This simplifies purification. Secreted recombinant polypeptide from a yeast host cell fermentation can be purified by methods analogous to those disclosed by Urdal et al., [J. Chromatog., 296:171, (1984)]. Urdal et al., describe two sequential, reversed-phase HPLC steps for purification of recombinant human IL-2 on a preparative HPLC column.

II. Interleukin 1β Protease Inhibitors

The inhibitors of the present invention are substituted compounds comprising an amino acid sequence of from 1 to about 5 amino acid residues having an N-terminal blocking group and a C-terminal Asp residue connected to an electronegative leaving group, wherein the amino acid sequence corresponds to at least a portion of the sequence Ala-Tyr-Val-His-Asp, which sequence represents the sequence of residues 112 to 116 of preIL-1β.

The amino acid sequence of preIL-1β is presented in Seq. I.D. No. 3 and in FIG. 2 taken from March, C. J. et al., Nature (London), 315(6021):641–647 (1985). Mature IL-1β is represented by the C-terminal 153 amino acid residues of preIL-1β. Thus, the N-terminal of IL-1β is the Ala residue at position 117 of Seq. I.D. No. 3.

Amino acid residues can be expressed by the full name (e.g., alanine) or by the three letter designation (e.g., Ala). This application will use the three letter designation.

The naturally occurring amino acids are the L isomers and are so indicated without any isomeric (e.g., L or D) designation. The D isomers are so indicated.

As used herein, the phrase "corresponds to" means that a particular sequence of an inhibitor compound may differ from the disclosed sequence by one or more conservative substitutions so long as such substitutions do not materially alter the inhibitory activity of the compounds of the present invention.

Examples of substitutions that do not materially alter inhibitory activity are replacement of the Ala at position 112 of Seq. I.D. No. 3 with Ser or Gly; replacement of the Tyr at position 113 of Seq. I.D. No. 3 with Phe; replacement of the Val at position 114 of Seq. I.D. No. 3 with Leu, Ile or Met and replacement of the His at position 115 of Seq. I.D. No. 3 with Phe, Pro, a positively charged amino acid such as Lys, Arg, His or Tyr, or the use of D isomers.

The C-terminal amino acid residue of the inhibitor compounds of the present invention is aspartic acid (Asp). Asp has a side chain of the formula $CH_2$-COOH. Preferably, the Asp side chain carboxyl group is protected to facilitate synthesis of the compounds of the present invention.

Asp side chain protection groups include, for example, a benzyl, substituted benzyl, formyl methyl or t-butyl moiety. The benzyl substituents increase the acid lability of the Asp side chain protecting moiety. Exemplary substituted benzyls are 2,4,6-trimethyl benzyl and 4-methoxybenzyl.

In a preferred embodiment, the Asp side chain protecting moiety is connected to the Asp side chain via an ester linkage, which linkage is subject to cleavage by naturally occurring intracellular esterase enzymes. In this way, the protected Asp with high lipid solubility gains access to a cell and is cleaved by an esterase to yield a charged, water soluble deprotected Asp that remains in the cytoplasm where IL-1$\beta$ pro is predominantly located.

As used herein, the phrase "N-terminal blocking group" refers to chemical groups attached to the amino group of the N-terminal amino acid residue of the sequences of the present invention. Such blocking groups are well known and readily apparent to those of skill in the art. The Peptides. ed. by Gross and Meienhofer, Academic Press, New York, pp. 3–81 (1981). N-terminal blocking groups have been utilized with other types of protease inhibitors. See, e.g., U.S. Pat. Nos. 4,652,552 and 4,636,492.

As used herein, the phrase "electronegative leaving group" refers to chemical groups susceptible to nucleophilic attack by an amino acid residue in the enzyme active site, thus modifying IL-1$\beta$ pro such that IL-1$\beta$ pro cannot interact with and cleave preIL-1$\beta$.

The compounds of the present invention inhibit the catalytic activity of IL-1$\beta$ pro in a reversible or an irreversible fashion. As used herein, "irreversible" means the formation of a covalent bond between the enzyme and the inhibitor.

The reversibility of IL-1$\beta$ pro activity is a function of the electronegative leaving group. When the electronegative leaving group is a diazoalkyl ketone, the inhibition of IL-1$\beta$ pro is irreversible and the compound is an irreversible inhibitor. When the electronegative leaving group is an aldehyde, the inhibition of IL-1$\beta$ pro is reversible and the compound is a reversible inhibitor.

The compounds of the present invention have the formula:

$$Z\text{-}Q_2\text{-AsP-}Q_1$$

where Z is an N-terminal blocking group; $Q_2$ is 0 to about 4 amino acids such that the sequence $Q_2$-Asp corresponds to at least a portion of the sequence Ala-Tyr-Val-His-Asp, residues 112 to 116 of Seq. I.D. No. 3; and $Q_1$ is an electronegative leaving group.

In a preferred embodiment, Z is $C_1$–$C_6$ alkyl, benzyl, acetyl, $C_1$–$C_6$ alkoxycarbonyl, benzyloxycarbonyl or $C_1$–$C_6$ alkyl carbonyl. As used herein, "alkyl" refers to linear or branched chains having 1 to 6 carbon atoms, which may be optionally substituted as herein defined. Representative alkyl groups include methyl, ethyl, propyl, isopropyl, butyl, pentyl, hexyl and the like. In a more preferred embodiment, Z is t-butoxycarbonyl (t-Boc), acetyl or benzyloxycarbonyl (Cbz).

$Q_2$ is preferably 1 amino acid. Preferably $Q_2$ is His, Phe, Pro, or Tyr. Most preferably, $Q_2$ is His or Phe.

$Q_1$ is preferably an aidehyde, a diazoalkyl ketone or a haloalkyl ketone. As used herein in reference to electronegative leaving groups, "alkyl" refers to linear or branched chain radicals having 1 to 3 carbon atoms, which may be optionally substituted as herein defined. Representative alkyl groups include methyl, ethyl, propyl and the like. More preferably, $Q_1$ is an aldehyde or fluoromethyl ($CH_2F$) ketone.

The compounds of the present invention are made by techniques generally corresponding to methods known and readily apparent to those of skill in the art. *See., e.g.,* Kettner, C. A. et al., *Arch. Biochem. Biophys.,* 162:56 (1974); U.S. Pat. Nos. 4,582,821; 4,644,055; Kettner, C. A. et al., *Arch. Biochem. Biophys.,* 165:739 (1974); Dakin, H. D. and West, R., *J. Biol. Chem.,* 78:91 (1928); Rasnick, D., *Anal. Blochem.,* 149:461 (1985).

Compounds having a fluoromethyl electronegative leaving group are preferably synthesized by the Rasnick procedure.

Compounds having a non-fluoro, haloalkyl ketone electronegative leaving group are synthesized in accordance with the Kettner procedure. An N-blocked amino acid or peptide is reacted with N-methylmorpholine and an alkyl, non-fluoro haloformate to generate a peptide-acid anhydride. The anhydride is then reacted with a diazoalkane in an inert, aprotonic solvent to form a peptide-diazomethane ketone. The diazomethane ketone is then reacted with an anhydrous solution of HCl, HBr or HI to produce the desired N-blocked, C-terminal haloalkyl ketone peptide or amino acid.

Compounds having a fluoroalkyl ketone electronegative leaving group are synthesized in accordance with a Rasnick procedure. An N-blocked peptide is reacted with fluoroacetic anhydride and a trialkylamine in an organic solvent to form a peptideanhydride. The anhydride is then reacted with a catalyst such as 4-dimethylaminopyridine and the reaction mixture maintained at about 25° C. for about two hours to allow for $CO_2$ evolution. The reaction mixture is then extracted with an organic solvent and the organic phase washed and dried. The organic solvent is removed to form an oil, which is then applied to a silica gel column. The N-blocked, fluoroalkyl ketone peptide is then eluted from the gel and purified.

Compounds having a fluoroalkyl ketone electronegative leaving group can be extended in the N-terminus direction by removing the N-terminal blocking group and coupling the deprotected compound with other protected amino acids. Bodanszky, The Practice of Peptide Synthesis, Springer-Verlag, Berlin (1984). Alternatively, deprotected compounds are acetylated to yield compounds having an N-terminal acetyl protecting group. Stewart et al., solid Phase Peptide Synthesis, Pierce Chemical Co., Rockford, Ill. (1984).

III. Methods of Treatment and Pharmaceutical Compositions

The present invention provides methods of using therapeutic compositions comprising an effective amount of IL-1$\beta$ pro polypeptides and derivatives thereof in a suitable diluent and carrier. For therapeutic use, purified IL-1$\beta$ pro or a biologically active derivative thereof is administered to a patient, preferably a human, for treatment in a manner appropriate to the indication. Thus, for example, IL-1$\beta$ pro compositions administered to suppress autoimmunity can be given by bolus injection, continuous infusion, sustained release from implants, or other suitable technique. Typically, an IL-1$\beta$ pro therapeutic agent will be administered in the form of a pharmaceutical composition comprising purified polypeptide in conjunction with physiologically acceptable carriers, excipients or diluents. Such carriers will be nontoxic to patients at the dosages and concentrations employed. Ordinarily, the preparation of such compositions entails combining IL-1β pro with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

The inhibitor compounds of the present invention are useful in inhibiting the physiological actions of interleukin 1μ by preventing formation of biologically active IL-1β. The inhibition of IL-1β pro results in a decrease in active IL-1β levels and a concomitant increase in preIL-1β, which compound is biologically inactive.

The inhibitor compounds of the present invention are also useful in treating dysfunctional states, such as autoimmune disease-associated inflammation, often mediated by increased IL-1 activity.

Mammals needing treatment for an inflammatory disorder or prevention of an autoimmune condition are administered effective amounts of the inhibitor compounds of this invention either alone or in the form of a pharmaceutical composition.

The pharmaceutical compositions of the present invention include one or more of the compounds of this invention formulated into compositions together with one or more non-toxic physiologically acceptable carriers, adjuvants or vehicles which are collectively referred to herein as carriers, for parenetral injection, for oral administration or solid or liquid form, for rectal or topical administration, and the like.

The compositions can be administered to humans and animals either orally, rectally, parenterally (intravenously, intramuscularly or subcutaneously) intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspension or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate of dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acadia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, caster oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any needed preservatives, buffers or propellants as may be required. Ophthalmic formulations, eye ointments, powders and solutions are also contemplated as being within the scope of this invention.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the IL-1β pro inhibiting compounds of the present invention, stabilizers, preservatives, excipients, and the like. The preferred lipids are the phospholipids and the phosphatidyl cholines (lecithins), both natural and synthetic.

Methods for form lipsomes are known in the art. See, for example, *Methods in Cell Biology*, Ed. by Prescott, Volume XIV, Academic Press, New York, N.Y. p.33 et seq., (1976).

Actual dosage levels of active ingredient in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the inhibitor compounds of this invention administered to a host in single or divided doses may be in amounts, for example, of from about 0.1 mg to about 160.0 mg per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The following examples are for the purposes of illustration and not by way of limitation.

EXAMPLES

EXAMPLE 1:

Substrate Specificity of IL-1β pro

This example illustrates the range of substrate specificity of purified human IL-1β pro enzyme to cleave a group of amino acid sequences. A variety of peptide substrates were prepared featuring changes in individual amino acids in the region corresponding to the cleavage site in human precursor IL-1β (His 115 to Pro 118). The reactivity of the peptide substrates was expressed relative to the peptide corresponding to Ala 112 to Set 121 of the precursor IL-1β sequence.

Substrate peptides were synthesized by solid phase method [Merrifield, *J. Amer. Chem. Soc.*, 86:304-05 (1964)] using either an Applied Biosystems 430A peptide synthesizer or by the manual T-bag approach of Houghten [*Proc. Nat. Acad. Sci. USA*, 82:5131-35 (1985)]. 4-Methyl henzhydrylamine resin was used. The substrate peptides were acteylated prior to cleavage from resin, by liquid (HF (0° C., 1 hr) in the presence of anisole as scavenger (HF:anisole 9:1). After evaporation of HF, the substrate peptide resin mixtures were washed with diethyl ether and extracted with 15% (w/v) acetic acid, lyophilized and purified on reverse phase high performance liquid chromatography (RP-HPLC) on a Vydac C18, 2.2 cm×25 cm column. Trifluoroacetic acid (0.1%) in water was solvent A and 0.1% trifluoroacetic acid in acetonitrile was solvent B for the mobile phases.

The purified substrate peptides were characterized by amino acid analysis using a Beckman 6300 system, RP-HPLC and mass spectrometry. Mass spectra were obtained by either fast atom bombardment on a VG Trio-2 system with xenon as the ionizing gas and glycerol/thioglycerol (1:1) as the sample matrix or by $^{252}$Cf plasma desorption mass spectrometry on a Bio-Ion 20 mass spectrometer (See Tsarbopoulos, *Peptide Res.* 2:258-66 (1989). In each case, the mass of the observed peptide substrate corresponded with the theoretical value.

Peptide solutions of standard concentration were prepared by dissolving about 2-3 mg of peptide substrate in water, loading the solution onto a Waters Sep-Pak C18 cartridge and washing three times with 5 ml of water. The peptide substrates were eluted with acetonitrile and then evaporated to dryness. Each substrate was standardized to 1 mM by amino acid analysis prior to use.

Purified human IL-1β pro enzyme (10 μl), peptide substrate in water (10 μl), and 10 mM Tris buffer, pH 8.0 containing 25% v/v glycerol (10 μl) were mixed and the mixtures were incubated at 37° C. for four hours. The reaction was quenched with by adding 1 M glycine/HCl buffer pH 2.0 (10 μl). The samples were then analyzed using RP-HPLC with a Vydac C18 column (0.46 cm×25 cm) and eluting with a linear gradient from 100% solvent A to 70% solvent A/30% solvent B over 30 minutes at a flow rate of 1 ml/min. The effluent was monitored at 280 nm absorbing product. A comparison of peak area of product peptide to that of total peak area of substrate and product yielded the extent of peptide cleavage, because the area under the combined substrate and product peaks was constant and independent of the amount of cleavage by the IL-1μ pro enzyme. Identities of peptide product peaks were confirmed by amino acid analysis and by mass spectrometry.

Table 1 shows the relative reactivities of a series of eight peptide substrates that were subject to digestion by purified IL-1β pro enzyme.

TABLE I

| Peptide | Sequence | Reactivity Relative To Peptide 1 |
|---|---|---|
| 1 | Ala—Tyr—Val—His—Asp—Ala—Pro—Val—Arg—Ser (Seq. I.D. No. 13) | 1.00 |

TABLE I-continued

| Peptide | Sequence | Reactivity Relative To Peptide 1 |
|---|---|---|
| 2 | Ala—Tyr—Val—His—Asn—Ala—Pro—Val—Arg—Ser (Seq. I.D. No. 14) | <0.01 |
| 3 | Ala—Tyr—Val—His—Glu—Ala—Pro—Val—Arg—Ser (Seq. I.D. No. 15) | <0.05 |
| 4 | Ala—Tyr—Val—His—(D—Asp)—Ala—Pro—Val—Arg—Ser (Seq. I.D. No. 16) | <0.01 |
| 5 | Ala—Tyr—Val—His—Asp—Gly—Pro—Val—Arg—Ser (Seq. I.D. No. 17) | 3.40 |
| 6 | Ala—Tyr—Val—His—Asp—Val—Pro—Val—Arg—Ser (Seq. I.D. No. 18) | <0.05 |
| 7 | Ala—Tyr—Val—Phe—Asp—Ala—Pro—Val—Arg—Ser (Seq. I.D. No. 19) | 0.50 |
| 8 | Ala—Tyr—Val—His—Asp—Ala—Ala—Val—Arg—Ser (Seq. I.D. No. 20) | 0.47 |

The cleavage site can be described with the corresponding human precursor IL-1β amino acid residues as follows:

P2 P1 P1' P2'

His-Asp-Ala-Pro

Changing the L-aspartic acid residue of peptide 1 to either asparagine (peptide 2), glutamic acid (peptide 3) or D-aspartate (peptide 4) has a profound effect on the ability of IL-1β pro to cleave the substrate. These data establish the requirement of an L-aspartate residue in the P1 position for this enzyme to be able to cleave a substrate.

Peptides 5 and 6 represent changes in the P1' position of the human precursor IL-1β cleavage site. Replacing alanine with glycine (peptide 5) results in a substrate that is 3.4 times more reactive than peptide 1. However, changing the same residue to a valine (peptide 6) effectively prevents proteolytic cleavage. The fact that with a glycine residue in P1' the peptide is cleaved more readily suggests that the alanine residue in human precursor IL-1β polypeptide is not critical for substrate binding, while the result with a valine residue in the P1' position indicates low steric tolerance at the P1' position. Thus, it seems unlikely that the IL-1β pro enzyme or derivatives thereof will cleave anywhere other than between Asp-Gly and Asp-Ala residues.

Peptides 7 and 8 represent changes to the P2 and P2' sites, respectively. Changing the proline of peptide I to an alanine yielded a substrate which was still cleaved by human IL-1β pro but only half as efficiently as the peptide with human IL-1β native sequence. A similar result was obtained when the histidine of peptide I was replaced with a phenylalanine. These data suggest that human IL-1β pro enzyme tolerates conservative replacements of both residues and that the P2 and P2' positions are not as vital for activity as the amino acids at the P1 and P1' positions.

EXAMPLE 2:

Effect of Substrate Length

This example illustrates the effect of substrate peptide length on the ability of human IL-1β pro enzyme to cleave peptide substrates. The experiment was conducted as described in Example 1. Five substrate peptides were made that correspond to the amino acid sequence of the IL-1β pro cleavage site of human precursor IL-1β. The results are shown in Table 2 below:

TABLE 2

| Peptide | Sequence | Reactivity Relative To Peptide 1 |
|---|---|---|
| 1 | Ala—Tyr—Val—His—Asp—Ala—Pro—Val—Arg—Ser— (Seq. I.D. No. 13) | 1.00 |
| 9 | Glu—Ala—Tyr—Val—His—Asp—Ala—Pro— (Seq. I.D. No. 21) | 0.74 |
| 10 | Tyr—Val—His—Asp—Ala—Pro—Val—Arg— (Seq. I.D. No. 22) | 2.40 |
| 11 | Val—His—Asp—Ala—Pro—Val— (Seq. I.D. No. 23) | Not cleaved |
| 12 | His—Asp—Ala—Pro— (Seq. I.D. No. 24) | Not cleaved |

The eight amino acid peptide (Ac-Tyr-Val-His-Asp-Ala-Pro-Val-Arg-NH2) is cleaved most efficiently while the four and six amino acid peptides are not cleaved. Thus, IL-1β pro has a minimum number of amino acid residues necessary for substrate peptide cleavage.

Example 3

Synthesis of IL-1β Protease Inhibitors

A. Synthesis of Boc-Asp-CH2F.

A suspension of Boc-Asp-OH (8.11 mmol) and fluoroacetic anhydride (16.2 mmol) in benzene (30 ml) was treated with triethylamine (16.2 mmol) at room temperature. The catalyst 4-dimethylaminopyridine (0.41 mmol) was added to the solution and the reaction stirred for about 2 h at room temperature. About 100 ml benzene was added to the reaction mixture. The organic solution was washed with 1N HCl (2×50 ml), saturated NaHCO3 (2×50 ml), and saturated NaCl (2×50 ml), followed by drying over anhydrous MgSO4. The solvent was then removed by evaporation under reduced pressure. The resulting oil was applied to a 2.5×80 cm column of silica gel (60–200 mesh). The title compound was eluted with 2% methanol in chloroform.

B. Synthesis of Boc-His-Asp-CH2F, Boc-Tyr-Asp-CHF and Boc-Phe-Asp-CH2F

Boc-Asp-CH2F prepared in accordance with the method of Example 3A above may be dissolved in trifluoroacetic acid (TFA) and the mixture stirred for about 5 minutes at about 23° C. Cold ether may then be added to the mixture. The ether is evaporated and toluene added to co-evaporate residual TFA. The deprotected peptide (H-Asp-CH2F) is obtained as a TFA salt. The deprotected peptide may then be coupled to a protected amino acid (i.e., Boc-HisOH, Boc-ProOH, Boc-TyrOH, Boc-PheOH) using a standard symmetric anhydride procedure employing dicyclohexylcarbodiimide as a coupling reagent. Bodanszky, *supra*.

C. Synthesis of Ac-His-Asp-CH2F, Ac-Pro-Asp-CH2F, Ac-Tyr-Asp-CH2F and Ac-Phe-Asp-CH2F.

The Boc protecting groups may be removed from the compounds made in accordance with the method of Example 3B using trifluoroacetic acid as described above. Each deprotected compound may then be acetylated with acetic anhydride and diisopropylamine (DIAE) according to standard techniques. Stuart et al., *supra.*

D. Synthesis of Cbz-His-Asp-CH$_2$F, Cbz-Pro-Asp-CH$_2$F, Cbz-Tyr-Asp-CH$_2$F and Cbz-Phe-Asp-CH$_2$F.

The Boc protecting group may be removed from Boc-Asp-CH$_2$F prepared according to the method of Example 3A using TFA as described above. Benzyloxycarbonyl-protected amino acids (i.e., Cbz-His-OH, Cbz-Phe-OH, Cbz-Tyr-OH, Cbz-Pro-OH) available from commercial sources (Bachem, Philadelphia, Pa.) can then be coupled to the deprotected Asp using a symmetric anhydride coupling procedure. Bodanszky, *supra.*

Example 4

Inhibition of IL-1β pro Activity

Boc-Asp-CH$_2$F was tested for its ability to inhibit IL-1β pro catalyzed degradation of preIL-Iβ using an in vitro assay method. Black, et al., *J. Biol. Chem.,* 263(19): 9437 (1988). The results of this study are shown in FIG. 2. Boc-Asp-CH$_2$F was prepared in accordance with the method of example of 1A.

A. Production of preIL-Iβ

Precursor preIL-1β polypeptide was obtained from *E. coli* using standard recombinant DNA techniques. Black, supra. Recombinant preIL-1β was expressed in *E. coli* under the control of the phage λ PL promoter and cI857$^{ts}$ thermolabile repressor. Using standard recombinant DNA techniques, pLNIL-1βF was constructed by ligating the following DNA segments: (I) 6160 base pairs of *Nco I/Hind* III-digested pLNIL-1β (12) containing the vector (conferring ampicillin resistance), codons 134–269 and 3' noncoding regions of HuIL-1β; (2) complementary synthetic oligonucleotides encoding residues 1–6 of IL-1β and *Nco* I and *Sst* I complementary ends; and (3) a 380-base pair *Sst I/- Hind* III restriction fragment from plasmid IL-1β-6(1) encoding residues 7–133. The ligation mixture was transformed into the tetracycline-resistant host RRI:pRK248cI$^{ts}$ (12) and correctly assembled plasmids were identified by restriction analysis of DNA isolated from transformants resistant to both ampicillin and tetracycline. Transformants containing pLNIL-1βF were tested for the production of preIL-1β by SDS-PAGE analysis of cultures grown in super induction medium to A$_{600}$ of 0.5 and derepressed for 1–20 h by elevation of temperature from 30° to 42° C. A protein of about 31,000 daltons was apparent in samples from pLNIL-IβF containing cultures but not in control cultures lacking the IL-1β coding region. Immuno-dot blot analysis with an anti-IL-1β monoclonal antibody (MAb) and purified recombinant mature IL-1β as a standard indicated that the cultures contained approximately 2.5–5.0 g/ml of preIL-1β.

B. Extraction of preIL-1β from *E. coli*

Cell pellets from 2.5 liters of transferred *E. coli* culture were resuspended in 20 ml of 30 mM Tris-HCl buffer (pH 9.5) containing 5 mM ethylenediaminetetraacetic acid (EDTA), 500 μg/ml of lysozyme, and 1 mM phenylmethanesulfonyl (PMSF). The cell suspensions were homogenized using a Polytron homogenizer (Brinkmann Instruments), rapidly frozen in a Dry Ice/methanol bath, and then thawed. Next, 200 ml of 30 mM Tris-HCl buffer (pH 8.0) containing 150 mM NaCl and 1 mM PMSF was added to the suspensions, which were then homogenized until a uniform homogenate was obtained. The suspensions were incubated for 30 minutes at 4° C., then centrifuged at 4° C. for 60 minutes at 3800× g. The supernatant fractions were carefully decanted and filtered to remove any particular matter. The pellets were re-extracted in 200 ml of 30 mM Tris-HCl buffer (pH 8.0), containing 150 mM NaCl, 8M urea, and 1 mM PMSF. Since both the Tris and the urea extracts contained substantial amounts of the preIL-1β, both were purified as described below.

C. Purification of preIL-Iβ

All chromatographic procedures were carried out at 4° C. All fractions were assayed for protein concentration, and conductivity was measured where appropriate. After each chromatographic step, fractions were analyzed by sodium dodecyl sulfate-polyacrylamide gel electrophoresis SDS-PAGE (with a 10–20% gradient of polyacrylamide), followed by silver staining, and by Western blot using a MAb generated against purified mature IL-1β.

The extracts were diluted 1:4 in H$_2$O, the pH was adjusted to 8.1, and the material was loaded at 100 ml/h onto a 25×2.5 cm Q-Sepharose column. For the Tris extract, the column was equilibrated in 10 mM Tris-HCl (pH 8.1). For the urea extract, the column was equilibrated in 10 mM Tris-HCl (pH 8.1), 2M urea. The columns were washed with 8 column volumes of 10 mM Tris-HCl (pH 8.1), and the bound proteins eluted with a linear gradient (three column volumes) ranging from 0 to 1.5M NaCl in 10 mM Tris-HCl (pH 8.1). Fractions of 7.5 ml were collected and stored at 4° C. until the next step of the purification.

The Q-Sepharose fractions containing the preIL-Iβ (as determined by Western blot analysis) were pooled and diluted 1:10 in 10 mM Tris-HCl (pH 8.1). The column was washed with 4 column volumes of the starting buffer.

The Tris-HCl solution was applied to a 20×5 cm column of phenyl-Sepharose CL-4B that had been equilibrated in 10 mM Tris HCl buffer (pH 8.1) containing 0.2M (NH$_4$)$_2$SO$_4$. The column was washed with 3 column volumes of the starting buffer and then material was eluted initially with 4 column volumes of a decreasing linear gradient of (NH$_4$)$_2$SO$_4$, generated with 0.2 and 0M solutions in 10 mM Tris-HCl buffer (pH 8.1). Finally, the material was eluted with 2 column volumes of 10 mM Tris-HCl (pH 8.1). Fractions containing partially purified preIL-1β were pooled, dialyzed against PBS, and stored at −70° C. until use.

D. Proteolytic Treatment of preIL-Iβ

5 l of preIL-1β (about 50 μg/ml in PBS) was mixed with 10 l of purified IL-1β pro (15–75 g/ml in PBS) and incubated at 37° C. for 30 minutes. The incubation was terminated by placing the samples on Dry Ice or by the addition of SDS sample buffer. PMSF was then added to a concentration of 1 mM, and the samples were dialyzed against water. After dialysis, the samples were concentrated to dryness in a Speed-Vac concentrator and dissolved in SDS sample buffer.

E. Western Blot Analysis of Proteolytic Products

SDS-PAGE was carried out with 12% polyacrylamide gels. The gels were placed in transfer buffer (0.192M glycine. 0.025M Tris-HCl (pH 8.3), 20% v/v methanol), and protein was then electrophoresed onto nitrocellulose (Sartorius) in a Hoeffer transfer apparatus (1 h at maximum voltage). The nitrocellulose was subsequently placed in 20 mM sodium phosphate, ph 7.4 (PBS) containing 3% bovine serum albumin for at least 15 minutes at room temperature. We used a MAb specific for mature IL-1β to probe the blot. MAb was added to a concentration of 9 μg/ml, and the incubation was continued for 30 minutes. The blot was then rinsed three times with PBS and was developed with a solution obtained by mixing 6 mg of horseradish peroxidase developing reagent (Bio-Rad) dissolved in 2 ml methanol and hydrogen peroxide (60 μl diluted into 10 ml of Tris-buffered saline).

The data show that Boc-Asp-Ch₂F completely inhibits the generation of mature IL-Iβ from preIL-1β at a concentration of 5 μM and partially inhibits generation of mature IL-1β at a concentration of 1 μM.

Example 5

Biological activity of IL-1β pro when transfected into COS-7 cells.

We inserted a cDNA corresponding to amino acids 120 to 404 into a mammalian cell expression vector (pDC303). This plasmid was co-transfected into COS-7 cells (monkey kidney) with a second mammalian expression plasmid containing a cDNA encoding precursor IL-1β. After two days, cells were radiolabeled with $^{35}S$ and IL-1β specific proteins were immunoprecipitated from cell lysates. The immunoprecipitates were analyzed by SDS-PAGE and autoradiography. We found that transfected COS-7 cells can process precursor IL-1β to mature IL-1β only if the cells were co-transfected with a plasmid encoding IL-1β pro. Cells co-transfected with a control plasmid or cells mock transfected did not show any processing of precursor IL-1β. Thus, IL-1β pro, lacking the N-terminal 119 amino acids enables cells to process precursor IL-1β to the mature form of this protein.

---

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 1659 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AAAAGGAGAG  AAAAGCCTAA  AAGAGAGTGG  GTAGATGGCC  GACAAGGTCC  TGAAGGAGAA    60
GAGAAAGCTG  TTTATCCGTT  CCATGGGTGA  AGGTACAATA  AATGGCTTAA  GGTAGAAGGT   120
GAAGGAAATA  CTGGATGAAT  TATTACAGAC  AAGGGTGCTG  AACAAGGAAG  AGATGGAGAA   180
AGTAAAACGT  GAAAATGCTA  CAGTTTATAG  AAAAGAAGAA  CGCTTATGGA  TAAGACCCGA   240
GCTTTGATTG  ACTCCGTTAT  TCCGAAAGGG  GCACAGGCAT  GCCAAATTTG  CATCACATAC   300
CGGATAAGTG  AAAGTGATAA  TTTGTGAAGA  AGACAGTTAC  CTGGCAGGGA  CGCTGGGACT   360
CTCAGCAGAT  CAAACATCTG  GAAATTACCT  TAATTGAGGA  AAGAAAGAAA  ATTATGCAAG   420
ACTCTCAAGG  AGTACTTTCT  TCCTTTCCAG  CTCCTCAGGC  AGTGCAGGAC  AACCCAGCTA   480
TGCCCACAGG  GAACGGAAGA  GTGAATCCTC  AGGCTCAGAA  GGGAATGTCA  AGCTTTGCTC   540
CCTAGAAGAA  GCTCAAAGGA  TATGGAAACA  AAAGTCGGCA  GTTAAGTAGA  ACAGGAGAGA   600
TTTATCCAAT  AATGGACAAG  TCAAGCCGCA  CACGTCTTGC  TCTCATTATC  TGCAATGAAG   660
AATTTGACAG  TAGAGTGAAG  AATGTTTGAG  TAATTCCTAG  AAGAACTGGA  GCTGAGGTTG   720
ACATCACAGG  CATGACAATG  CTGCTACAAA  ATCTGGGGTA  CAGCGTAAAA  TAAATTTGGA   780
AAAAGGGATG  TGAAAAAAAA  TCTCACTGCT  TCGGACATGA  CTACAGAGCT  GGAGGCATTT   840
GCACACCGCC  CAGAGCACAA  GTATATGAGG  GCGGACCTCT  GACAGCACGT  TCCTGGTGTT   900
CATGTCTCAT  GGTATTCGGG  AAGGCATTTG  TGGGAAGAAA  CACTCTGAGG  AAGAAAATAT   960
ACACAAGTCC  CAGATATACT  ACAACTCAAT  GCAATCTTTA  ACATGTTGAA  TACCAAGAAC  1020
TGCCCAAGTT  TGAAGGACAG  AACAGGAGAA  TAAGAAACCG  AAGGTGATCA  TCATCCAGGC  1080
CTGCCGTGGT  GACAGCCCTG  GTGTGGTGTG  GTTTAAAGAT  TCAGTAGGAA  GATTGGGAAA  1140
```

-continued

```
AAAGGTTTCT GGAAACCTAT CTTTACCAAC TACAGAAGAG TTTGAGGATG ATGCTATTAA  1200
GAAAGCCCAC ATAGAAGAA AACTAAATAG TTGAGATTTT ATCGCTTTCT GCTCTTCCAC  1260
ACCAGATAAT GTTTCTTGGA GACATCCAC AATGGGCTCT GTTTTATTG AGGTGGTAAC  1320
CAAGGAGAAG GGAAGACTCA TTGAACATAT GCAAGAATAT GCCTGTTCCT GTGATGTGGA  1380
GGAAATTTTC CGCAAGGTTC GATTTGGAGA GAAGTTTGAG ATTAGCTTCA TTTGAGCAGC  1440
CAGATGGTAG AGCGCAGATG CCCACCACTG AAAGAGTGAC TTTGACAAGA TGTTTCTACC  1500
TCGTTCCCAG GACATTAAAA TAAGGAAACT GTATGAATGT CTGCGGGCAG GAAGTGAAGA  1560
GATCGTTCTG TAAAAGGTTT TTGGAATTAT GTCTGCTGAA TAATAAACTT TTTTTGAAAT  1620
AATAAATCTG GTAGAAAAAT GAAAAAAAAA AAAAAAAA  1659
```

( 2 ) INFORMATION FOR SEQ ID NO: 2:

( i ) SEQUENCE CHARACTERISTICS:
        ( A ) LENGTH: 404 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Met Ala Asp Lys Val Leu Lys Glu Lys Arg Lys Leu Phe Ile Arg Ser
  1               5                  10                  15
Met Gly Glu Gly Thr Ile Asn Gly Leu Leu Asp Glu Leu Leu Gln Thr
                 20                  25                  30
Arg Val Leu Asn Lys Glu Glu Met Glu Lys Val Lys Arg Glu Asn Ala
                 35                  40                  45
Thr Val Met Asp Lys Thr Arg Ala Leu Ile Asp Ser Val Ile Pro Lys
         50                  55                  60
Gly Ala Gln Ala Cys Gln Ile Cys Ile Thr Tyr Ile Cys Glu Glu Asp
 65                  70                  75                  80
Ser Tyr Leu Ala Gly Thr Leu Gly Leu Ser Ala Asp Gln Thr Ser Gly
                 85                  90                  95
Asn Tyr Leu Asn Met Gln Asp Ser Gln Gly Val Leu Ser Ser Phe Pro
                100                 105                 110
Ala Pro Gln Ala Val Gln Asp Asn Pro Ala Met Pro Thr Ser Ser Gly
                115                 120                 125
Ser Glu Gly Asn Val Lys Leu Cys Ser Leu Glu Glu Ala Gln Arg Ile
        130                 135                 140
Trp Lys Gln Lys Ser Ala Glu Ile Tyr Pro Ile Met Asp Lys Ser Ser
145                 150                 155                 160
Arg Thr Arg Leu Ala Leu Ile Ile Cys Asn Glu Glu Phe Asp Ser Ile
                165                 170                 175
Pro Arg Arg Thr Gly Ala Glu Val Asp Ile Thr Gly Met Thr Met Leu
                180                 185                 190
Leu Gln Asn Leu Gly Tyr Ser Val Asp Val Lys Lys Asn Leu Thr Ala
                195                 200                 205
Ser Asp Met Thr Thr Glu Leu Glu Ala Phe Ala His Arg Pro Glu His
        210                 215                 220
Lys Thr Ser Asp Ser Thr Phe Leu Val Phe Met Ser His Gly Ile Arg
225                 230                 235                 240
Glu Gly Ile Cys Gly Lys Lys His Ser Glu Gln Val Pro Asp Ile Leu
                245                 250                 255
Gln Leu Asn Ala Ile Phe Asn Met Leu Asn Thr Lys Asn Cys Pro Ser
                260                 265                 270
Leu Lys Asp Lys Pro Lys Val Ile Ile Ile Gln Ala Cys Arg Gly Asp
```

|     |     |     |     | 275 |     |     |     |     | 280 |     |     |     |     | 285 |     |
| --- | --- | --- | --- | --- | --- | --- | --- | --- | --- | --- | --- | --- | --- | --- | --- |
| Ser | Pro | Gly | Val | Val | Trp | Phe | Lys | Asp | Ser | Val | Gly | Val | Ser | Gly | Asn |
|     | 290 |     |     |     | 295 |     |     |     |     | 300 |     |     |     |     |     |
| Leu | Ser | Leu | Pro | Thr | Thr | Glu | Glu | Phe | Glu | Asp | Asp | Ala | Ile | Lys | Lys |
| 305 |     |     |     |     | 310 |     |     |     |     | 315 |     |     |     |     | 320 |
| Ala | His | Ile | Glu | Lys | Asp | Phe | Ile | Ala | Phe | Cys | Ser | Ser | Thr | Pro | Asp |
|     |     |     |     | 325 |     |     |     |     | 330 |     |     |     |     | 335 |     |
| Asn | Val | Ser | Trp | Arg | His | Pro | Thr | Met | Gly | Ser | Val | Phe | Ile | Gly | Arg |
|     |     |     | 340 |     |     |     |     | 345 |     |     |     |     | 350 |     |     |
| Leu | Ile | Glu | His | Met | Gln | Glu | Tyr | Ala | Cys | Ser | Cys | Asp | Val | Glu | Glu |
|     |     |     | 355 |     |     |     |     | 360 |     |     |     | 365 |     |     |     |
| Ile | Phe | Arg | Lys | Val | Arg | Phe | Ser | Phe | Glu | Gln | Pro | Asp | Gly | Arg | Ala |
|     |     | 370 |     |     |     |     | 375 |     |     |     |     | 380 |     |     |     |
| Gln | Met | Pro | Thr | Thr | Glu | Arg | Val | Thr | Leu | Thr | Arg | Cys | Phe | Tyr | Leu |
| 385 |     |     |     |     | 390 |     |     |     |     | 395 |     |     |     |     | 400 |
| Phe | Pro | Gly | His |     |     |     |     |     |     |     |     |     |     |     |     |

( 2 ) INFORMATION FOR SEQ ID NO: 3:

( i ) SEQUENCE CHARACTERISTICS:
        ( A ) LENGTH: 269 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 3:

| Met | Ala | Glu | Val | Pro | Glu | Leu | Ala | Ser | Glu | Met | Met | Ala | Tyr | Tyr | Ser |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gly | Asn | Glu | Asp | Asp | Leu | Phe | Phe | Glu | Ala | Asp | Gly | Pro | Lys | Gln | Met |
|     |     |     | 20  |     |     |     |     | 25  |     |     |     |     | 30  |     |     |
| Lys | Cys | Ser | Phe | Gln | Asp | Leu | Asp | Leu | Cys | Pro | Leu | Asp | Gly | Gly | Ile |
|     |     | 35  |     |     |     |     | 40  |     |     |     |     | 45  |     |     |     |
| Gln | Leu | Arg | Ile | Ser | Asp | His | Tyr | Ser | Lys | Gly | Phe | Arg | Gln | Ala |     |
|     | 50  |     |     |     |     | 55  |     |     |     |     | 60  |     |     |     |     |
| Ala | Ser | Val | Val | Val | Ala | Met | Asp | Lys | Leu | Arg | Lys | Met | Leu | Val | Pro |
| 65  |     |     |     |     | 70  |     |     |     |     | 75  |     |     |     |     | 80  |
| Cys | Pro | Gln | Thr | Phe | Gln | Glu | Asn | Asp | Leu | Ser | Thr | Phe | Phe | Pro | Phe |
|     |     |     |     | 85  |     |     |     |     | 90  |     |     |     |     | 95  |     |
| Ile | Phe | Glu | Glu | Glu | Pro | Ile | Phe | Phe | Asp | Thr | Trp | Asp | Asn | Glu | Ala |
|     |     |     |     | 100 |     |     |     |     | 105 |     |     |     |     | 110 |     |
| Tyr | Val | His | Asp | Ala | Pro | Val | Arg | Ser | Leu | Asn | Cys | Thr | Leu | Arg | Asp |
|     |     |     | 115 |     |     |     |     | 120 |     |     |     |     | 125 |     |     |
| Ser | Gln | Gln | Lys | Ser | Leu | Val | Met | Ser | Gly | Pro | Tyr | Glu | Leu | Lys | Ala |
|     | 130 |     |     |     |     | 135 |     |     |     |     | 140 |     |     |     |     |
| Leu | His | Leu | Gln | Gly | Gln | Asp | Met | Glu | Gln | Gln | Val | Val | Phe | Ser | Met |
| 145 |     |     |     |     | 150 |     |     |     |     | 155 |     |     |     |     | 160 |
| Ser | Phe | Val | Gln | Gly | Glu | Glu | Ser | Asn | Asp | Lys | Ile | Pro | Val | Ala | Leu |
|     |     |     |     | 165 |     |     |     |     | 170 |     |     |     |     | 175 |     |
| Gly | Leu | Lys | Glu | Lys | Asn | Leu | Tyr | Leu | Ser | Cys | Val | Leu | Lys | Asp | Asp |
|     |     |     | 180 |     |     |     |     | 185 |     |     |     |     | 190 |     |     |
| Lys | Pro | Thr | Leu | Gln | Leu | Glu | Ser | Val | Asp | Pro | Lys | Asn | Tyr | Pro | Lys |
|     |     | 195 |     |     |     |     | 200 |     |     |     |     | 205 |     |     |     |
| Lys | Lys | Met | Glu | Lys | Arg | Phe | Val | Phe | Asn | Lys | Ile | Glu | Ile | Asn | Asn |
|     | 210 |     |     |     |     | 215 |     |     |     |     | 220 |     |     |     |     |
| Lys | Leu | Glu | Phe | Glu | Ser | Ala | Gln | Phe | Pro | Asn | Trp | Tyr | Ile | Ser | Thr |
| 225 |     |     |     |     | 230 |     |     |     |     | 235 |     |     |     |     | 240 |

| Ser | Gln | Ala | Glu | Asn | Met | Pro | Val | Phe | Leu | Gly | Gly | Thr | Lys | Gly | Gly |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Gln | Asp | Ile | Thr | Asp | Phe | Thr | Met | Gln | Phe | Val | Ser | Ser |
|-----|-----|-----|-----|-----|-----|-----|-----|-----|-----|-----|-----|-----|
|     |     |     | 260 |     |     |     |     | 265 |     |     |     |     |

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 4:

TACCGGCTGT TCCAGGAC    18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 5:

TACCTATTCT GGGCTCGA    18

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 6:

TTGGTCGATA CGGGTGT    17

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 7:

CACCACACCA AATTTCTA    18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 8:

ATGGAGAAGG GTCCTGTA    18

( 2 ) INFORMATION FOR SEQ ID NO:9:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 9:

GTCGAATTCA AYCCNGCNAT GCCNAC      26

( 2 ) INFORMATION FOR SEQ ID NO:10:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 10:

GTCTCTAGAA GYTTNACRTT NCCYTC      26

( 2 ) INFORMATION FOR SEQ ID NO:11:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 11:

ATATCGGTAC CGCCTCCAGC ATGCCTCCGG CAATGCCCAC ATC      43

( 2 ) INFORMATION FOR SEQ ID NO:12:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 12:

CTGCTAGATC TGCCCGCAGA CATTCATACA G      31

( 2 ) INFORMATION FOR SEQ ID NO: 13:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 13:

Ala Tyr Val His Asp Ala Pro Val Arg Ser
 1               5                  10

( 2 ) INFORMATION FOR SEQ ID NO: 14:

( i ) SEQUENCE CHARACTERISTICS:
    ( A ) LENGTH: 10 amino acids
    ( B ) TYPE: amino acid
    ( D ) TOPOLOGY: linear -continued (i i) MOLECULE TYPE: peptide (x i) SEQUENCE DESCRIPTION: SEQ ID NO: 14:

Ala Tyr Val His Asn Ala Pro Val Arg Ser
1               5                   10

(2) INFORMATION FOR SEQ ID NO: 15:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO: 15:

Ala Tyr Val His Glu Ala Pro Val Arg Ser
1               5                   10

(2) INFORMATION FOR SEQ ID NO: 16:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (i x) FEATURE:
        (B) LOCATION: 4
        (C) IDENTIFICATION METHOD: Xaa = D-Asp (x i) SEQUENCE DESCRIPTION: SEQ ID NO: 16:

Ala Tyr Val His Xaa Ala Pro Val Arg Ser
1               5                   10

(2) INFORMATION FOR SEQ ID NO: 17:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO: 17:

Ala Tyr Val His Asp Gly Pro Val Arg Ser
1               5                   10

(2) INFORMATION FOR SEQ ID NO: 18:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO: 18:

Ala Tyr Val His Asp Val Pro Val Arg Ser
1               5                   10

(2) INFORMATION FOR SEQ ID NO: 19:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO: 19:

```
Ala  Tyr  Val  Phe  Asp  Ala  Pro  Val  Arg  Ser
1                 5                           10
```

( 2 ) INFORMATION FOR SEQ ID NO: 20:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 20:

```
Ala  Tyr  Val  His  Asp  Ala  Ala  Val  Arg  Ser
1                 5                           10
```

( 2 ) INFORMATION FOR SEQ ID NO: 21:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 21:

```
Glu  Ala  Tyr  Val  His  Asp  Ala  Pro  Val  Arg  Ser  Leu
1                      5                           10
```

( 2 ) INFORMATION FOR SEQ ID NO: 22:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 22:

```
Tyr  Val  His  Asp  Ala  Pro  Val  Arg
1                 5
```

( 2 ) INFORMATION FOR SEQ ID NO: 23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 23:

```
Val  His  Asp  Ala  Pro  Val
1                 5
```

( 2 ) INFORMATION FOR SEQ ID NO: 24:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 24:

```
His  Asp  Ala  Pro
1
```

What is claimed is:

a. a DNA insert selected from the group consisting of the nucleotide sequences in Seq. I.D. No. 1 beginning at nucleotide 1 and extending to nucleotide 1232, beginning at nucleotide 375 and extending to nucleotide 1232, and beginning at nucleotide 375 and extending to a nucleotide from about 851 to about 962;

b. DNA sequences which detectably hybridize to one or more of the foregoing DNA inserts and which encode or express a polypeptide displaying biological activity to proteolytically cleave human precursor IL-1β polypeptide at a cleavage site between Asp 116 and Ala 117 residues; or c. DNA sequences which, due to the degeneracy of the generic code, encode a mammalian IL-1β protease polypeptide encoded by any of the foregoing DNA inserts and sequences.

2. A recombinant expression vector comprising a DNA sequence according to claim 1.

3. A process for preparing a mammalian IL-1β protease enzyme or an analog or derivative thereof, comprising culturing a suitable host cell comprising a vector according to claim 2 under conditions promoting expression.

* * * * *

UNITED STATES PATENT AND TRADEMARK OFFICE
CERTIFICATE OF CORRECTION

PATENT NO.   : 5,416,013
DATED        : May 16, 1995
INVENTOR(S)  : Black et al

It is certified that error appears in the above-identified patent and that said Letters Patent is hereby corrected as shown below:

Column 43, line 1, claim 1, insert the following preamble:

1. The isolated DNA sequence encoding a mammalian interleukin 1 Beta (IL-1β) protease enzyme, wherein the DNA sequence comprises:"

Signed and Sealed this

Seventeenth Day of June, 1997

BRUCE LEHMAN

*Attest:*

*Attesting Officer*    *Commissioner of Patents and Trademarks*